(12) United States Patent
Kim

(10) Patent No.: US 8,868,215 B2
(45) Date of Patent: Oct. 21, 2014

(54) APPARATUS AND METHODS FOR MINIMALLY INVASIVE OBESITY TREATMENT

(75) Inventor: Daniel H. Kim, Houston, TX (US)

(73) Assignee: GEP Technology, Inc., Pleasantion, CA (US)

( * ) Notice: Subject to any disclaimer, the term of this patent is extended or adjusted under 35 U.S.C. 154(b) by 147 days.

(21) Appl. No.: 13/055,395

(22) PCT Filed: Jul. 13, 2009

(86) PCT No.: PCT/US2009/050429
§ 371 (c)(1),
(2), (4) Date: May 18, 2011

(87) PCT Pub. No.: WO2010/006341
PCT Pub. Date: Jan. 14, 2010

(65) Prior Publication Data
US 2011/0213448 A1    Sep. 1, 2011

Related U.S. Application Data

(60) Provisional application No. 61/080,175, filed on Jul. 11, 2008, provisional application No. 61/134,827, filed on Jul. 14, 2008.

(51) Int. Cl.
| | | |
|---|---|---|
| *A61N 1/06* | (2006.01) |
| *A61N 1/05* | (2006.01) |
| *A61M 25/00* | (2006.01) |
| *A61M 25/10* | (2013.01) |
| *A61F 5/00* | (2006.01) |
| *A61B 17/34* | (2006.01) |
| *A61N 1/36* | (2006.01) |

(52) U.S. Cl.
CPC ......... *A61N 1/0517* (2013.01); *A61M 25/0017* (2013.01); *A61M 25/1002* (2013.01); *A61F 5/003* (2013.01); *A61B 17/3468* (2013.01); *A61F 5/0026* (2013.01); *A61N 1/36007* (2013.01); *A61F 5/0069* (2013.01); *A61F 5/0073* (2013.01); *A61F 5/0003* (2013.01); *A61M 2025/1072* (2013.01); *A61N 1/36114* (2013.01)
USPC ............................................. 607/133; 607/40

(58) Field of Classification Search
CPC    A61N 1/36007; A61N 1/0507; A61N 1/0509
USPC ........................................... 607/40, 133, 124
See application file for complete search history.

(56) References Cited

U.S. PATENT DOCUMENTS

| | | |
|---|---|---|
| 4,052,978 A | 10/1977 | Eugenio |
| 4,917,092 A | 4/1990 | Todd et al. |

(Continued)

FOREIGN PATENT DOCUMENTS

| | | |
|---|---|---|
| WO | 2008058028 A2 | 5/2008 |
| WO | 2008063486 A2 | 5/2008 |

OTHER PUBLICATIONS

"Mechanisms of Disease", published in The New England Journal of Medicine to Franklin H. Epstein, MD vol. 336, No. 12, Mar. 27, 1997.*

(Continued)

*Primary Examiner* — Paula J Stice
(74) *Attorney, Agent, or Firm* — Patterson & Sheridan, L.L.P.

(57) ABSTRACT

Apparatus and methods are provided for the effective and minimally invasive treatment of obesity. In one embodiment, a device for providing therapy to a patient includes an inflatable structure adapted and configured for positioning at least partially within a gastroesophageal (GE) space formed between an inner wall of a phrenoesophageal ligament (POL) and outer walls of the esophagus and cardiac orifice and an electrode structure adapted and configured for positioning at least partially within the GE space. In another embodiment, a method for treating a patient includes introducing an electrode at least partially into a gastroesophageal (GE) space formed between an inner wall of a phrenoesophageal ligament (POL) and outer walls of the esophagus and cardiac orifice and modulating tissue using the electrode.

21 Claims, 33 Drawing Sheets

(56) References Cited

U.S. PATENT DOCUMENTS

| | | | |
|---|---|---|---|
| 5,147,294 A | 9/1992 | Smith et al. | |
| 5,263,480 A | 11/1993 | Wernicke et al. | |
| RE34,502 E | 1/1994 | Webster, Jr. | |
| 5,454,840 A | 10/1995 | Krakovsky et al. | |
| 5,522,854 A | 6/1996 | Ideker et al. | |
| 5,725,471 A | 3/1998 | Davey et al. | |
| 5,753,651 A | 5/1998 | dePadova | |
| 5,897,505 A | 4/1999 | Feinberg et al. | |
| 6,086,525 A | 7/2000 | Davey et al. | |
| 6,301,492 B1 | 10/2001 | Zonenshayn | |
| 6,334,442 B1 | 1/2002 | Altamura | |
| 6,348,423 B1 | 2/2002 | Griffiths et al. | |
| 6,356,787 B1 | 3/2002 | Rezai et al. | |
| 6,438,423 B1 | 8/2002 | Rezai et al. | |
| 6,470,892 B1 | 10/2002 | Forsell | |
| 6,500,110 B1 | 12/2002 | Davey et al. | |
| 6,587,719 B1 | 7/2003 | Barrett et al. | |
| 6,609,025 B2 | 8/2003 | Barrett et al. | |
| 6,611,715 B1 | 8/2003 | Boveja | |
| 6,701,185 B2 | 3/2004 | Burnett et al. | |
| 6,721,603 B2 | 4/2004 | Zabara et al. | |
| 6,758,219 B2 | 7/2004 | Sapala et al. | |
| 6,759,063 B2 | 7/2004 | Almada | |
| 6,879,859 B1 | 4/2005 | Boveja | |
| 6,885,888 B2 | 4/2005 | Rezai | |
| 6,928,320 B2 | 8/2005 | King | |
| 6,937,896 B1 | 8/2005 | Kroll | |
| 6,950,707 B2 | 9/2005 | Whitehurst | |
| 7,077,821 B2 | 7/2006 | Durgin | |
| 7,167,750 B2 | 1/2007 | Knudson et al. | |
| 7,184,828 B2 | 2/2007 | Hill et al. | |
| 7,200,443 B2 | 4/2007 | Faul | |
| 7,236,822 B2 | 6/2007 | Dobak, III | |
| 7,239,912 B2 | 7/2007 | Dobak, III | |
| 7,263,405 B2 | 8/2007 | Boveja et al. | |
| 7,266,410 B2 | 9/2007 | Chen | |
| 7,299,091 B2 | 11/2007 | Barrett et al. | |
| 7,310,557 B2 | 12/2007 | Maschino et al. | |
| 7,337,005 B2 | 2/2008 | Kim et al. | |
| 7,340,306 B2 | 3/2008 | Barrett et al. | |
| 7,416,551 B2 * | 8/2008 | Ad | 606/41 |
| 7,477,945 B2 | 1/2009 | Rezai et al. | |
| 7,483,746 B2 | 1/2009 | Lee et al. | |
| 7,489,969 B2 | 2/2009 | Knudson et al. | |
| 7,494,661 B2 | 2/2009 | Sanders | |
| 7,499,752 B2 | 3/2009 | Maschino et al. | |
| 7,529,582 B1 | 5/2009 | DiLorenzo | |
| 8,187,297 B2 * | 5/2012 | Makower et al. | 606/192 |
| 8,295,945 B1 * | 10/2012 | Thacker et al. | 607/117 |
| 2001/0016725 A1 * | 8/2001 | Valley et al. | 604/509 |
| 2002/0072738 A1 * | 6/2002 | Edwards et al. | 606/41 |
| 2002/0193851 A1 | 12/2002 | Silverman et al. | |
| 2003/0018367 A1 | 1/2003 | DiLorenzo | |
| 2003/0054015 A1 | 3/2003 | Haze et al. | |
| 2003/0144708 A1 | 7/2003 | Starkebaum | |
| 2003/0144709 A1 | 7/2003 | Zabara et al. | |
| 2003/0158583 A1 | 8/2003 | Burnett et al. | |
| 2003/0181958 A1 | 9/2003 | Dobak | |
| 2004/0024428 A1 | 2/2004 | Barrett et al. | |
| 2004/0039427 A1 | 2/2004 | Barrett et al. | |
| 2004/0111118 A1 | 6/2004 | Hill et al. | |
| 2004/0162594 A1 | 8/2004 | King | |
| 2004/0193229 A1 | 9/2004 | Starkebaum et al. | |
| 2004/0230255 A1 | 11/2004 | Dobak | |
| 2004/0236381 A1 | 11/2004 | Dinsmoor et al. | |
| 2004/0236382 A1 | 11/2004 | Dinsmoor et al. | |
| 2004/0248188 A1 | 12/2004 | Sanders | |
| 2005/0003976 A1 | 1/2005 | Haze et al. | |
| 2005/0021092 A1 | 1/2005 | Yun et al. | |
| 2005/0021101 A1 | 1/2005 | Chen et al. | |
| 2005/0049655 A1 | 3/2005 | Boveja et al. | |
| 2005/0065562 A1 | 3/2005 | Rezai | |
| 2005/0065573 A1 | 3/2005 | Rezai | |
| 2005/0065575 A1 | 3/2005 | Dobak | |
| 2005/0070974 A1 | 3/2005 | Knudson et al. | |
| 2005/0075678 A1 | 4/2005 | Faul | |
| 2005/0131486 A1 | 6/2005 | Boveja et al. | |
| 2005/0131487 A1 | 6/2005 | Boveja et al. | |
| 2005/0137644 A1 | 6/2005 | Boveja et al. | |
| 2005/0158264 A1 | 7/2005 | Haze et al. | |
| 2005/0222635 A1 | 10/2005 | Krakovsky | |
| 2005/0222637 A1 | 10/2005 | Chen | |
| 2005/0245986 A1 | 11/2005 | Starkebaum | |
| 2006/0004414 A1 | 1/2006 | Chen | |
| 2006/0050914 A1 * | 3/2006 | Urso et al. | 381/328 |
| 2006/0052826 A1 | 3/2006 | Kim et al. | |
| 2006/0052827 A1 | 3/2006 | Kim et al. | |
| 2006/0052828 A1 | 3/2006 | Kim et al. | |
| 2006/0052835 A1 | 3/2006 | Kim et al. | |
| 2006/0052836 A1 | 3/2006 | Kim et al. | |
| 2006/0052837 A1 | 3/2006 | Kim et al. | |
| 2006/0052838 A1 | 3/2006 | Kim et al. | |
| 2006/0052839 A1 | 3/2006 | Kim et al. | |
| 2006/0052856 A1 | 3/2006 | Kim et al. | |
| 2006/0058376 A1 | 3/2006 | Moritani et al. | |
| 2006/0074450 A1 | 4/2006 | Boveja et al. | |
| 2006/0085046 A1 | 4/2006 | Rezai et al. | |
| 2006/0089571 A1 | 4/2006 | Gertner | |
| 2006/0095088 A1 | 5/2006 | De Ridder | |
| 2006/0111754 A1 | 5/2006 | Rezai et al. | |
| 2006/0116736 A1 | 6/2006 | DiLorenzo | |
| 2006/0116737 A1 | 6/2006 | Libbus | |
| 2006/0129028 A1 | 6/2006 | Krakousky | |
| 2006/0129201 A1 | 6/2006 | Lee et al. | |
| 2006/0155344 A1 | 7/2006 | Rezai et al. | |
| 2006/0161217 A1 | 7/2006 | Jaax et al. | |
| 2006/0167498 A1 | 7/2006 | DiLorenzo | |
| 2006/0190053 A1 | 8/2006 | Dobak | |
| 2006/0229274 A1 | 10/2006 | Hsue | |
| 2006/0247718 A1 | 11/2006 | Starkebaum | |
| 2006/0247719 A1 * | 11/2006 | Maschino et al. | 607/40 |
| 2006/0247721 A1 | 11/2006 | Maschino et al. | |
| 2006/0247722 A1 | 11/2006 | Maschino et al. | |
| 2006/0259077 A1 | 11/2006 | Pardo et al. | |
| 2007/0025608 A1 | 2/2007 | Armstrong | |
| 2007/0027483 A1 | 2/2007 | Maschino et al. | |
| 2007/0027486 A1 | 2/2007 | Armstrong | |
| 2007/0027497 A1 | 2/2007 | Parnis | |
| 2007/0049988 A1 | 3/2007 | Carbunaru et al. | |
| 2007/0093870 A1 | 4/2007 | Maschino | |
| 2007/0106337 A1 | 5/2007 | Errico et al. | |
| 2007/0106338 A1 | 5/2007 | Errico | |
| 2007/0106339 A1 | 5/2007 | Errico et al. | |
| 2007/0135846 A1 | 6/2007 | Knudson et al. | |
| 2007/0162084 A1 | 7/2007 | Chen et al. | |
| 2007/0162085 A1 | 7/2007 | DiLorenzo | |
| 2007/0203521 A1 | 8/2007 | Dobak et al. | |
| 2007/0203531 A9 | 8/2007 | Starkebaum | |
| 2007/0219596 A1 | 9/2007 | Dobak | |
| 2007/0225768 A1 | 9/2007 | Dobak | |
| 2008/0009913 A1 | 1/2008 | Errico et al. | |
| 2008/0033511 A1 | 2/2008 | Dobak | |
| 2008/0051824 A1 | 2/2008 | Gertner | |
| 2008/0058878 A1 | 3/2008 | King | |
| 2008/0086182 A1 | 4/2008 | Ben-David et al. | |
| 2008/0132968 A1 | 6/2008 | Starkebaum | |
| 2008/0147137 A1 | 6/2008 | Cohen et al. | |
| 2008/0147139 A1 | 6/2008 | Barrett et al. | |
| 2008/0167695 A1 | 7/2008 | Tehrani et al. | |
| 2008/0183237 A1 | 7/2008 | Errico et al. | |
| 2008/0208266 A1 | 8/2008 | Lesser et al. | |
| 2008/0262411 A1 | 10/2008 | Dobak | |
| 2008/0269833 A1 | 10/2008 | Scott et al. | |
| 2008/0269834 A1 | 10/2008 | Byerman et al. | |
| 2008/0281372 A1 | 11/2008 | Libbus et al. | |
| 2008/0293830 A1 | 11/2008 | Katagiri et al. | |
| 2008/0319274 A1 | 12/2008 | Ballegaard et al. | |

(56) References Cited

U.S. PATENT DOCUMENTS

2009/0118777 A1    5/2009   Iki et al.
2009/0118780 A1    5/2009   DiLorenzo
2009/0254143 A1*   10/2009  Tweden et al. .................. 607/40

OTHER PUBLICATIONS

Al-Motabagani, M.A.H.—"An Anatomical Study of the Phrenoesophageal Ligament," IndMedica—Journal of the Anatomical Society of India, vol. 51, No. 1 (Jan. 2002-Jun. 2002), 7 pages.

PCT International Search Report and Written Opinion for Application PCT/US2009/050429, dated Oct. 29, 2009.

Supplemental EPO Search Report for European Application No. 09795291.5, dated Jul. 8, 2011.

Lointier et al: "Chirurgie laparoscopique 1-6 de 1 'obesite morbide". EMC—Chirurgie, Elsevier, vol. 2, No. 1, Feb. 1, 2005, pp. 1-49, XP025396381. ISSN: 1762-570X.

\* cited by examiner

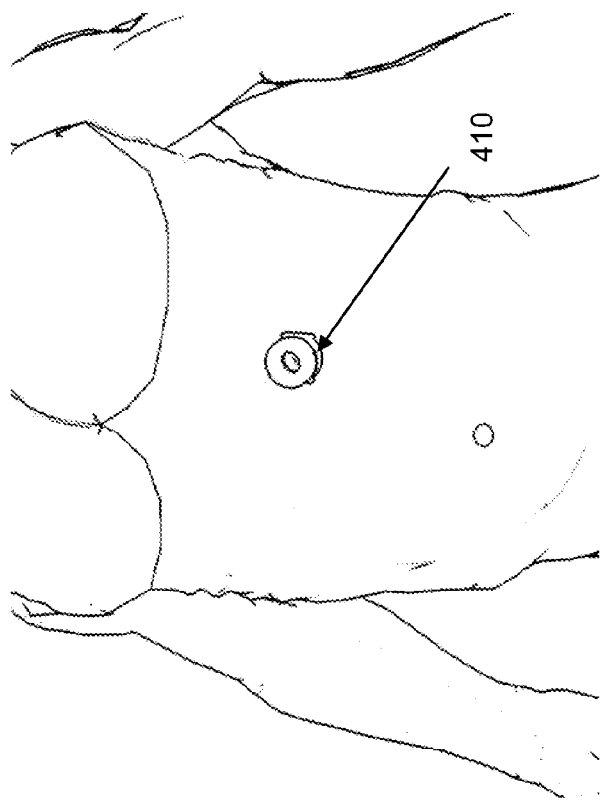
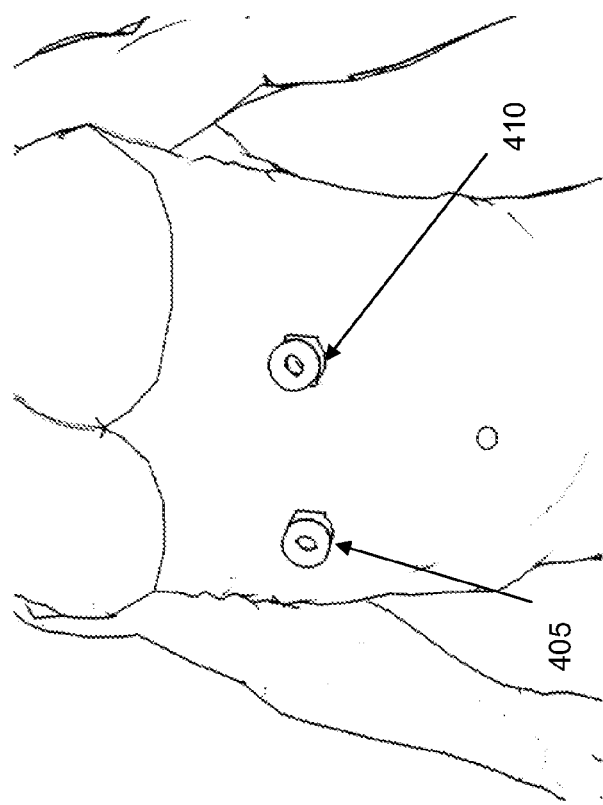

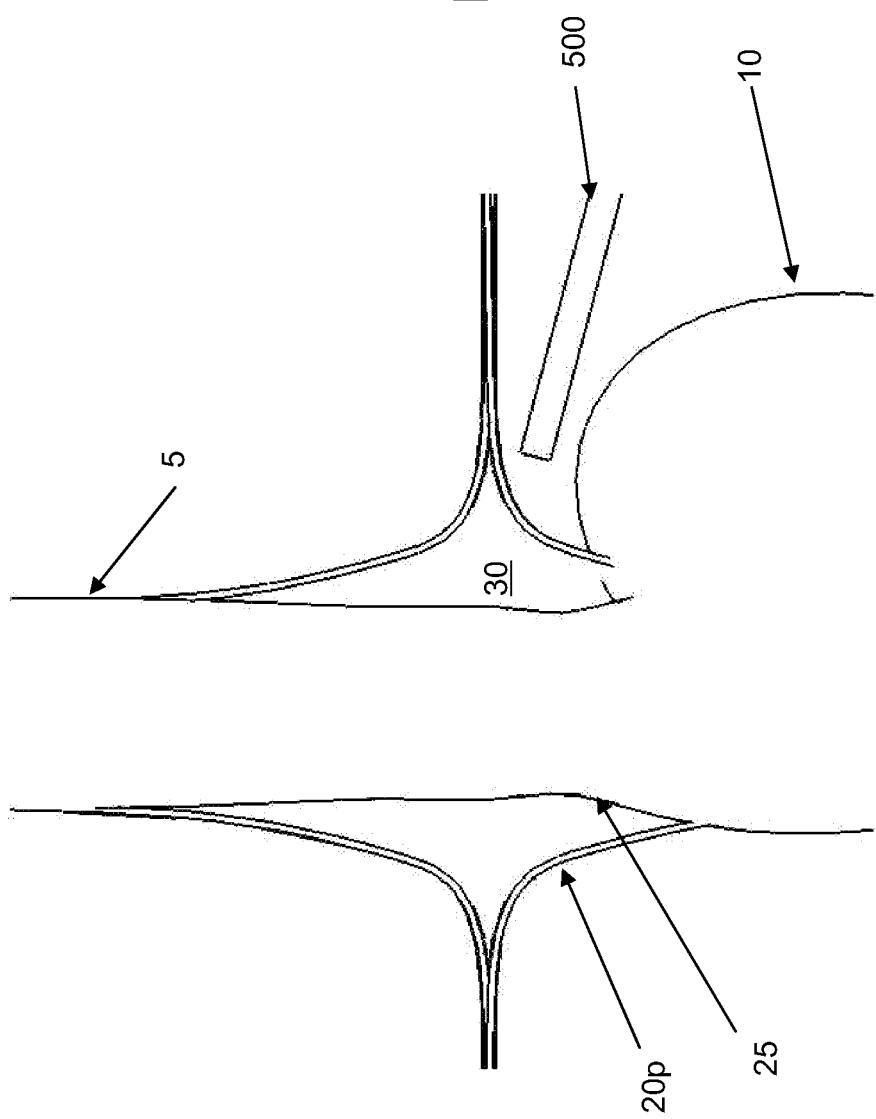

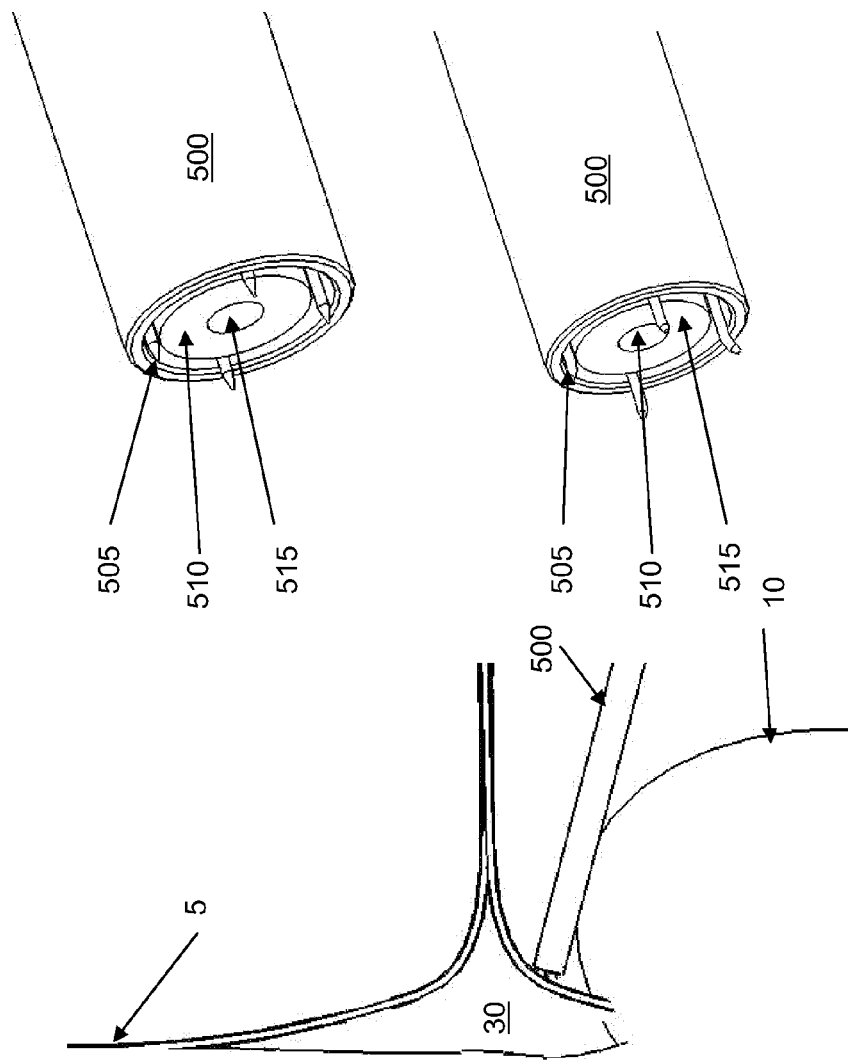
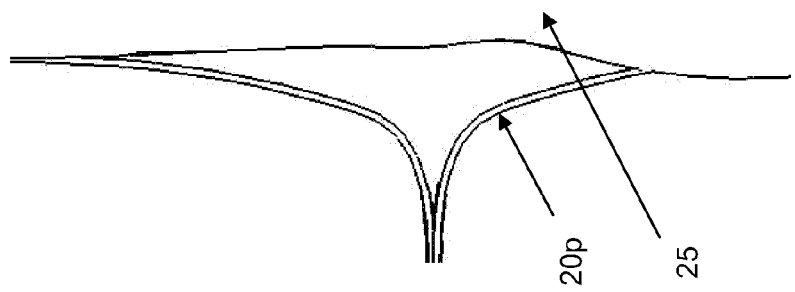

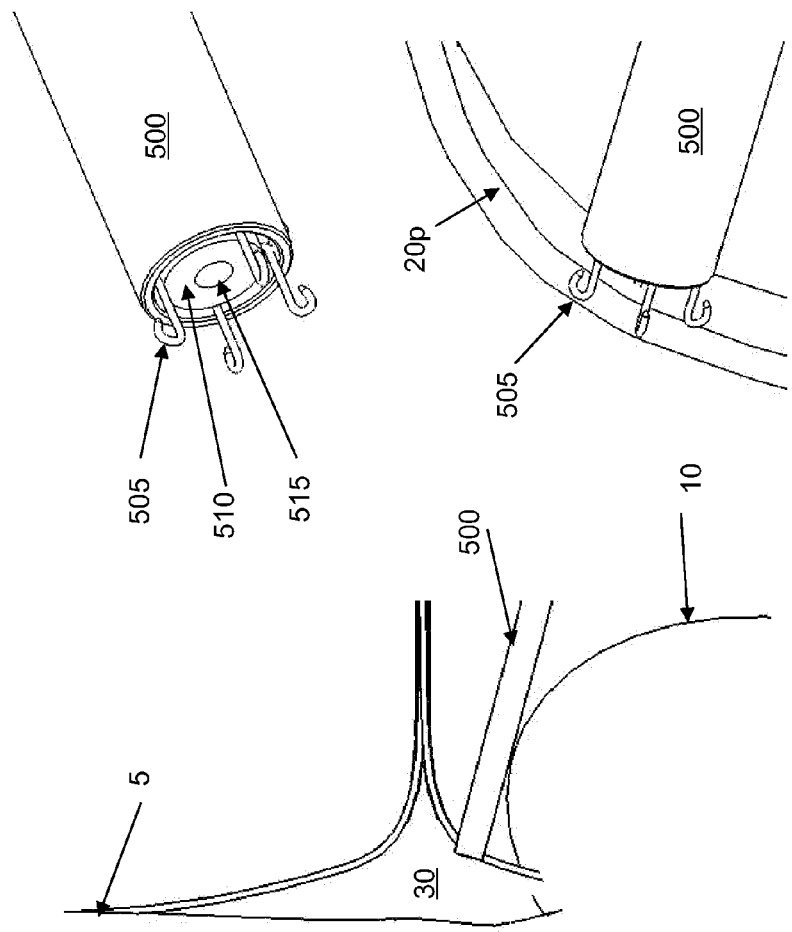
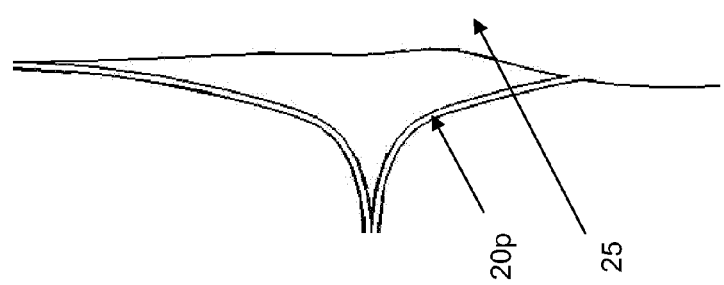

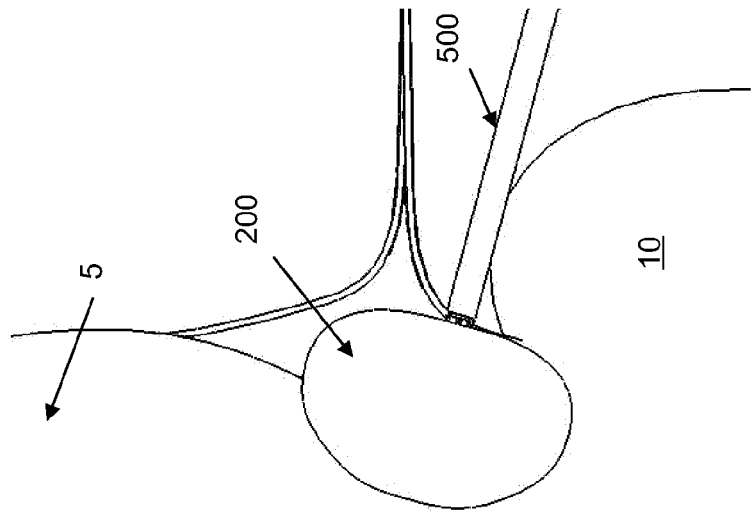
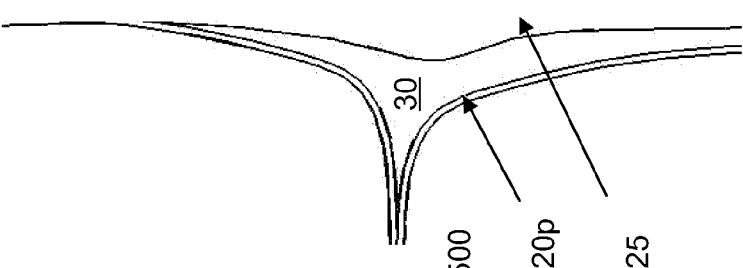
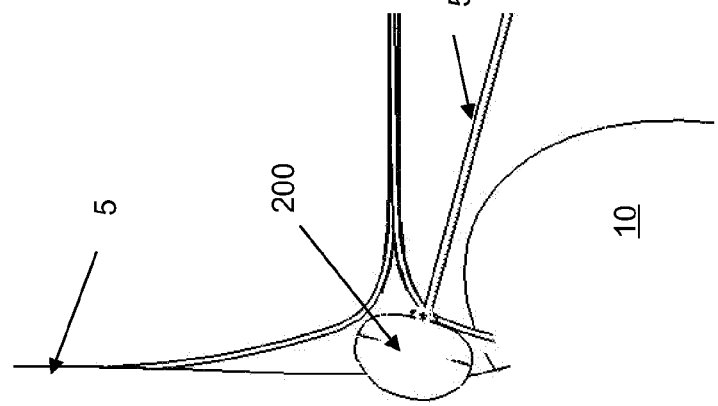
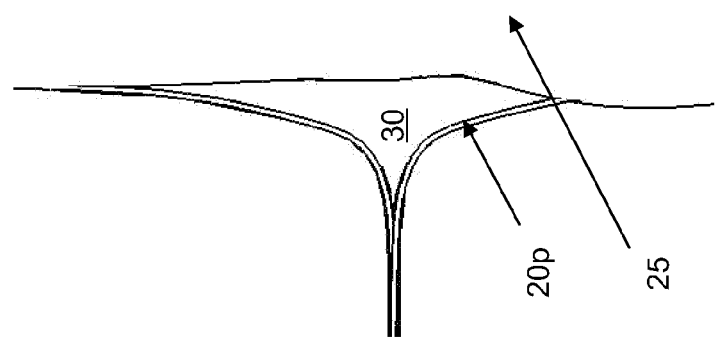

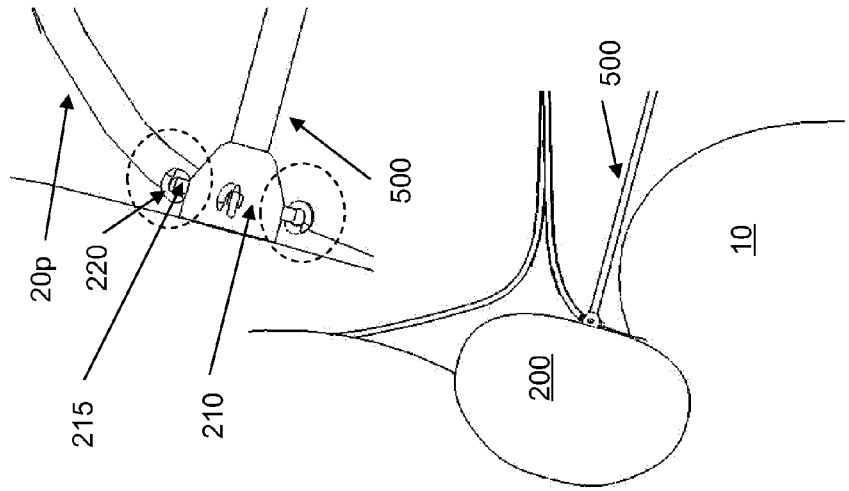
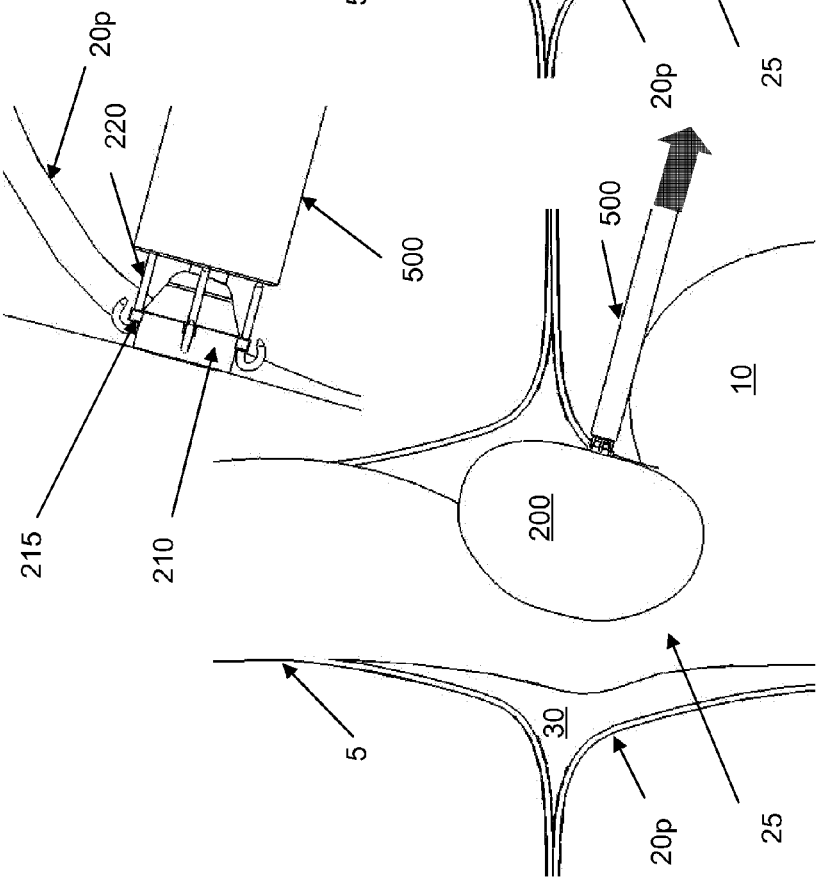

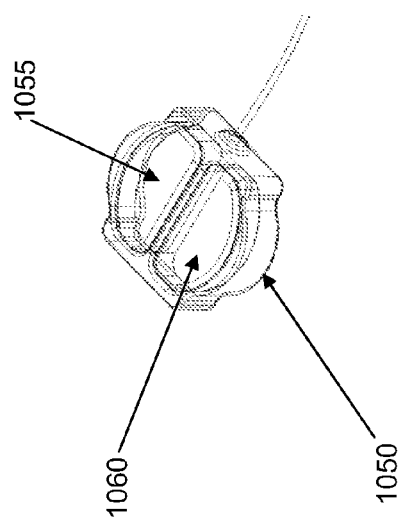
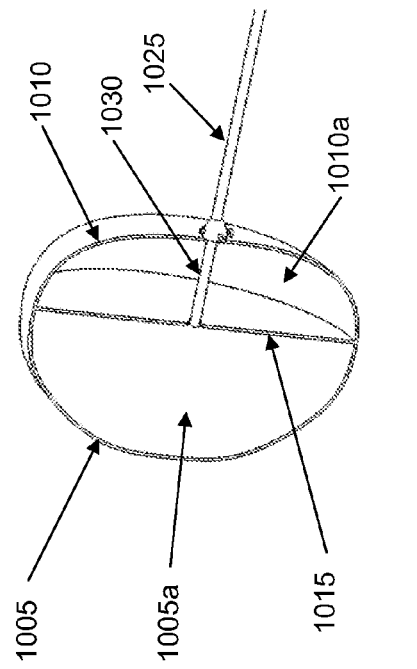
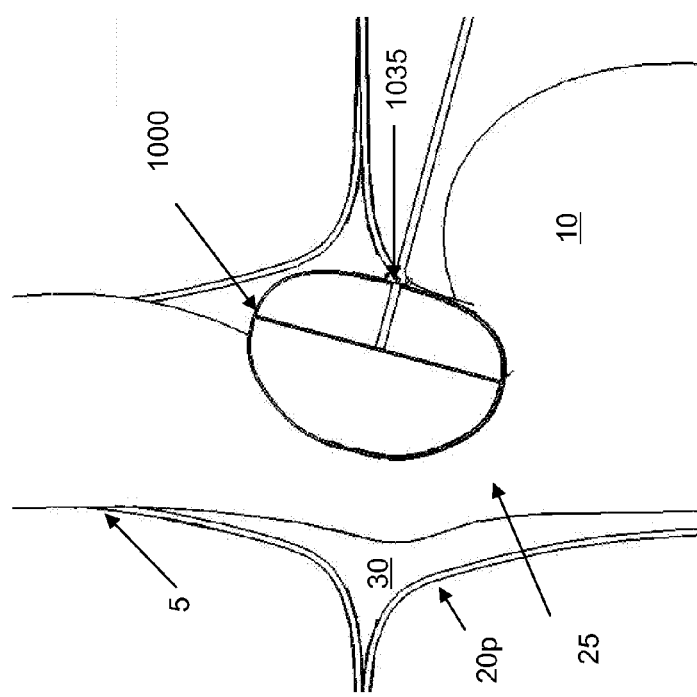
FIG. 10B
FIG. 10C
FIG. 10A

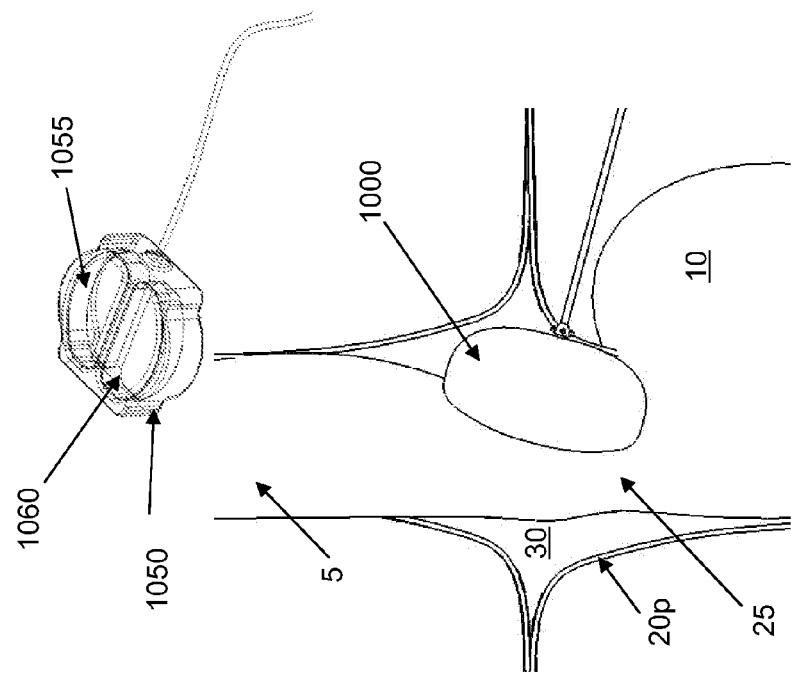
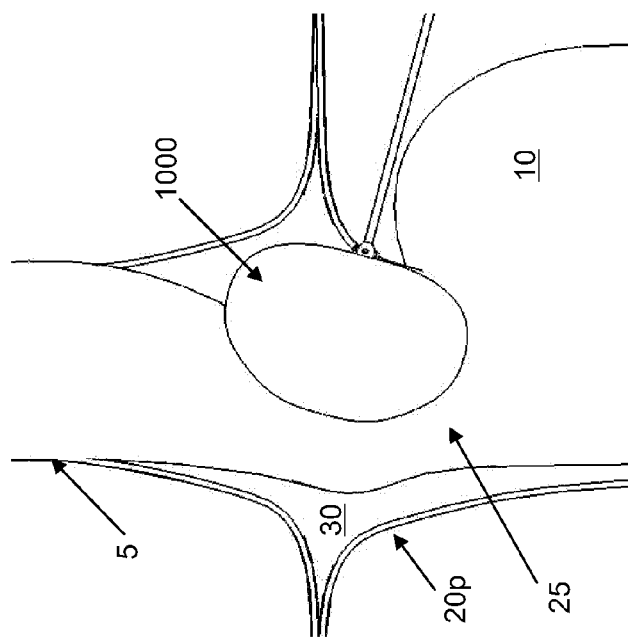

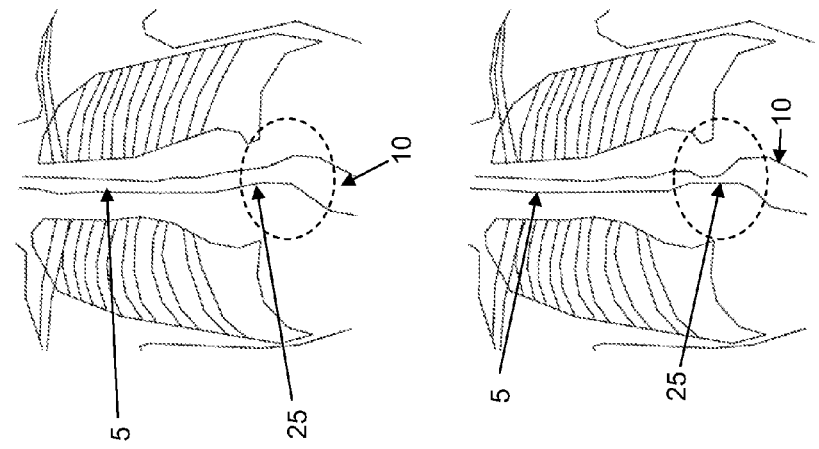
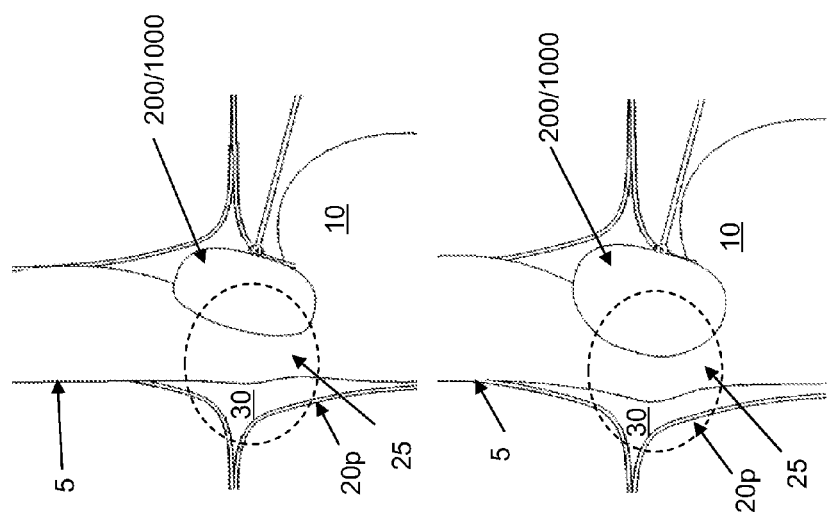

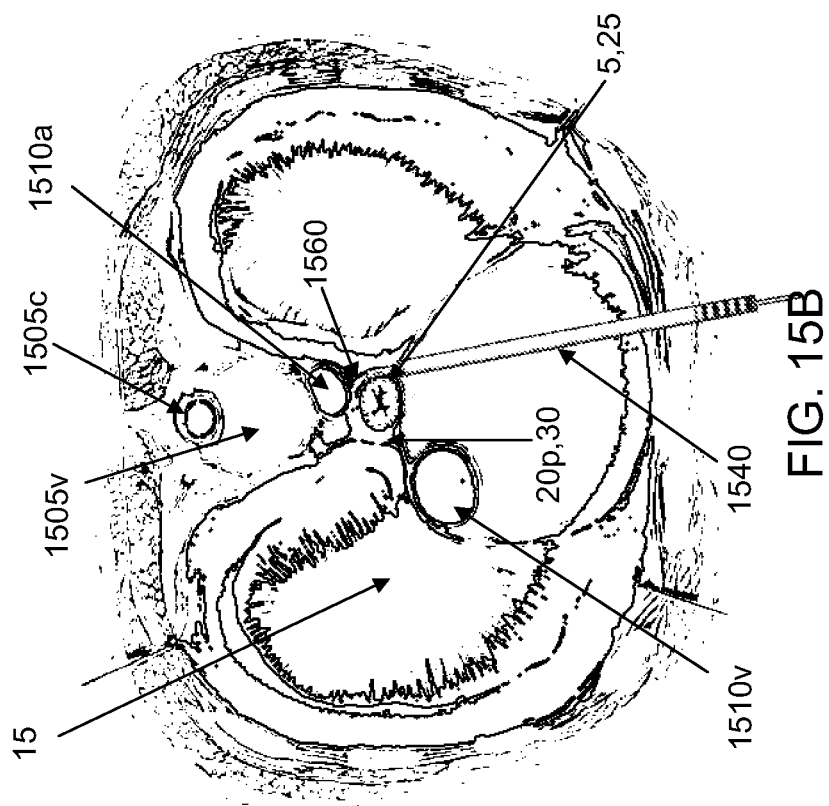
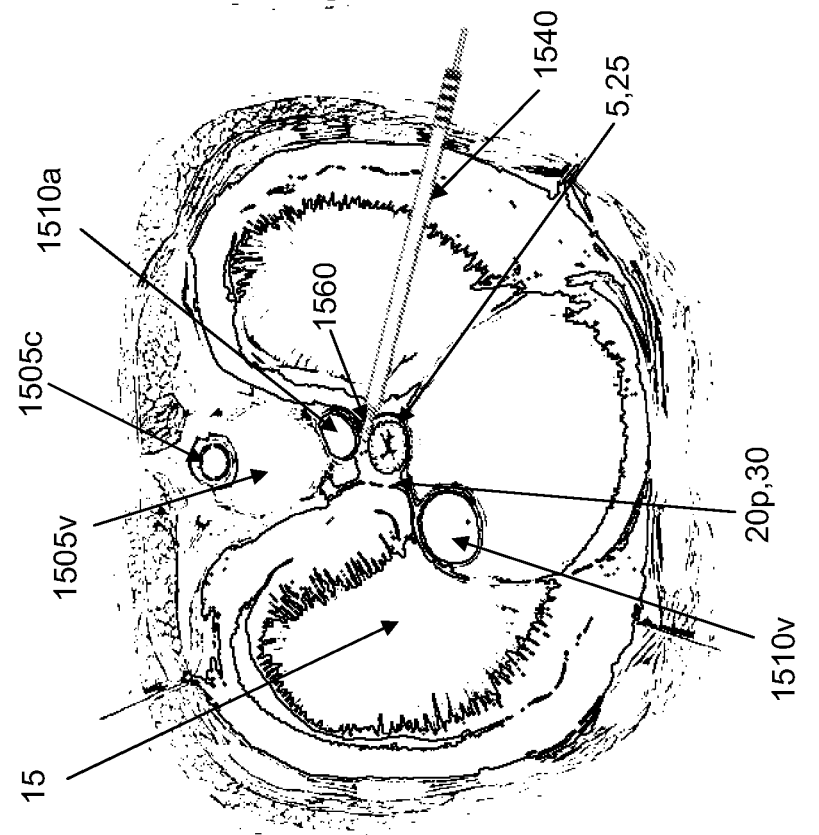

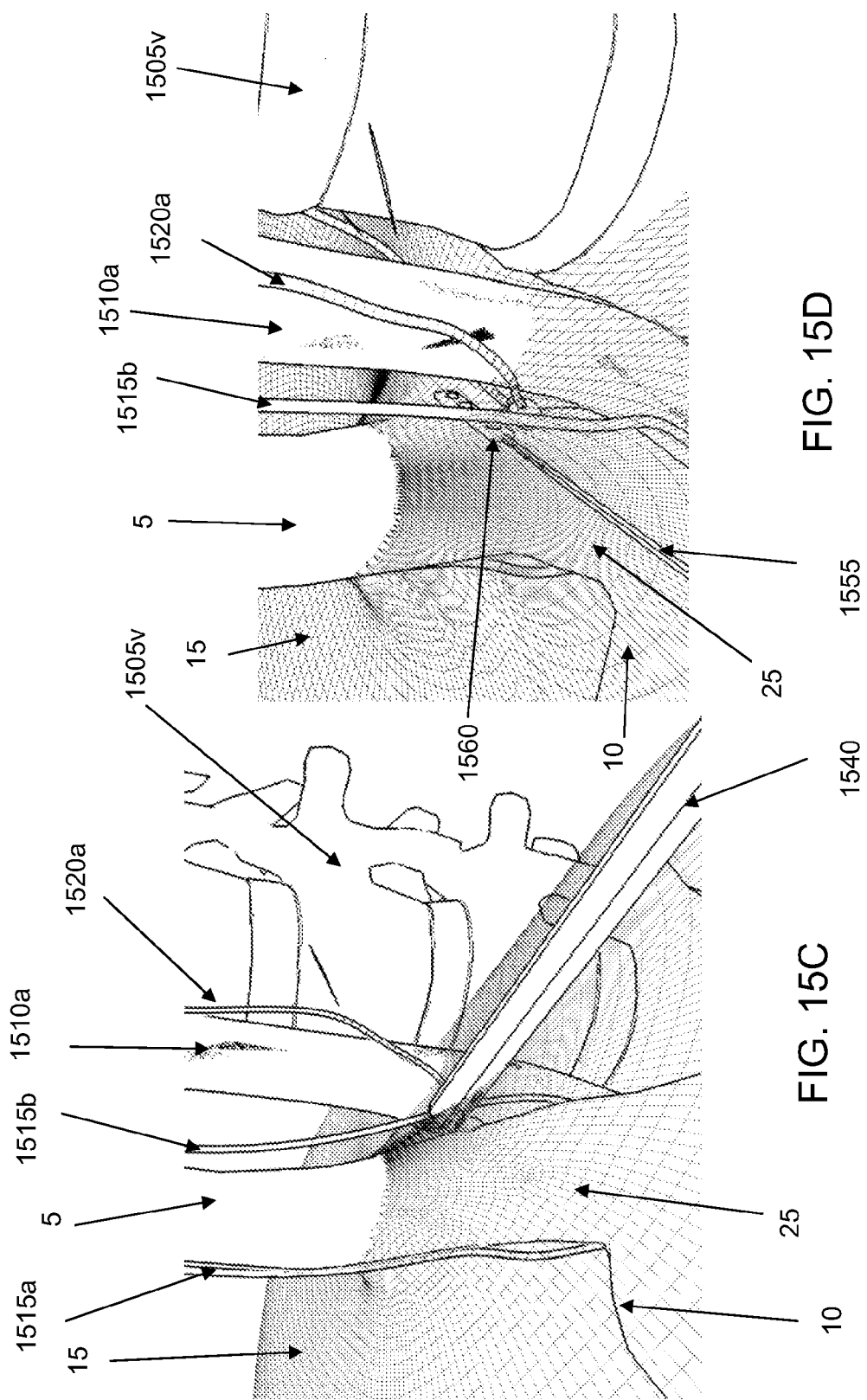

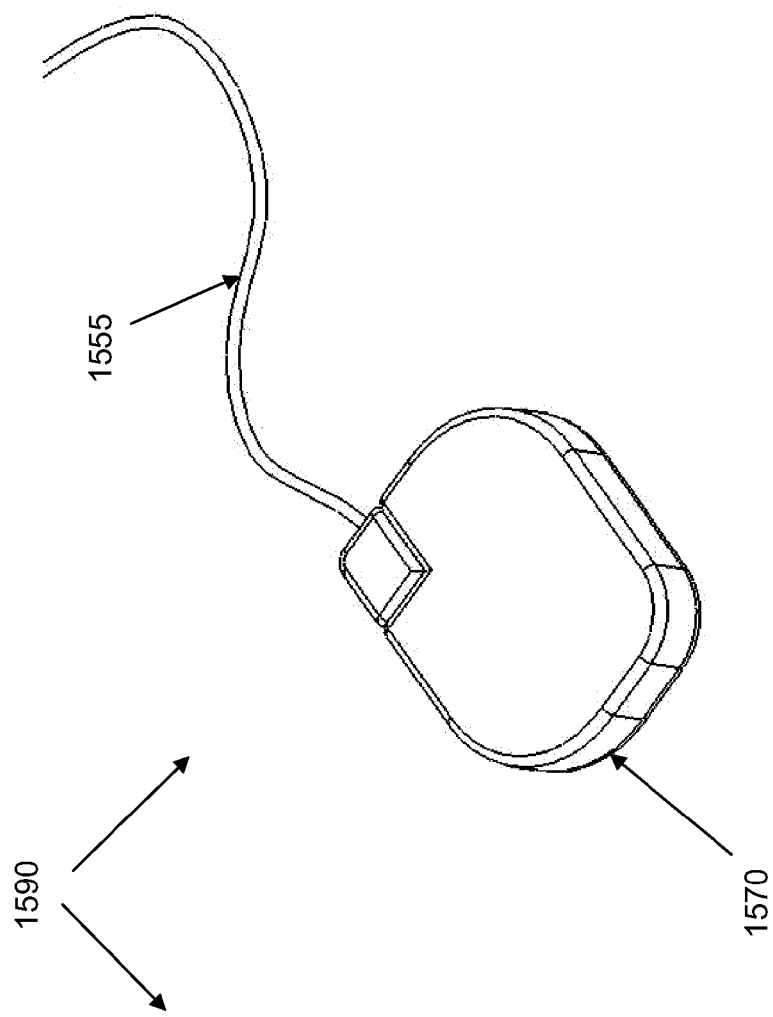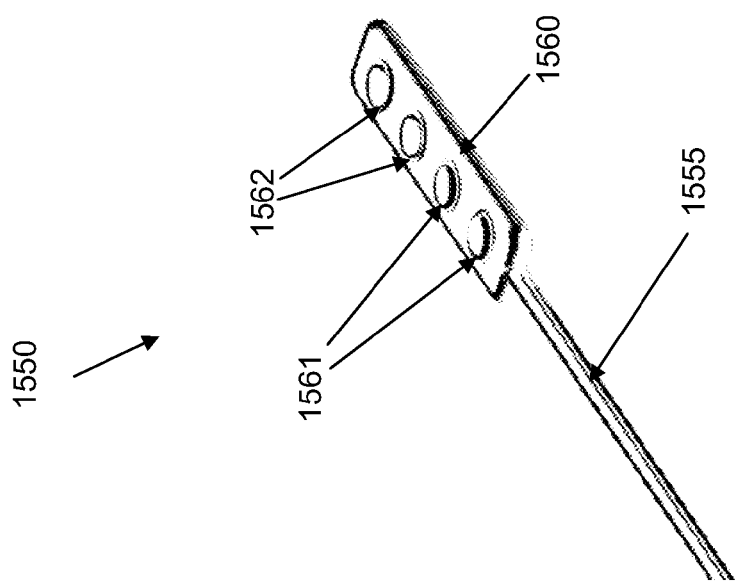
FIG. 16B
FIG. 16A

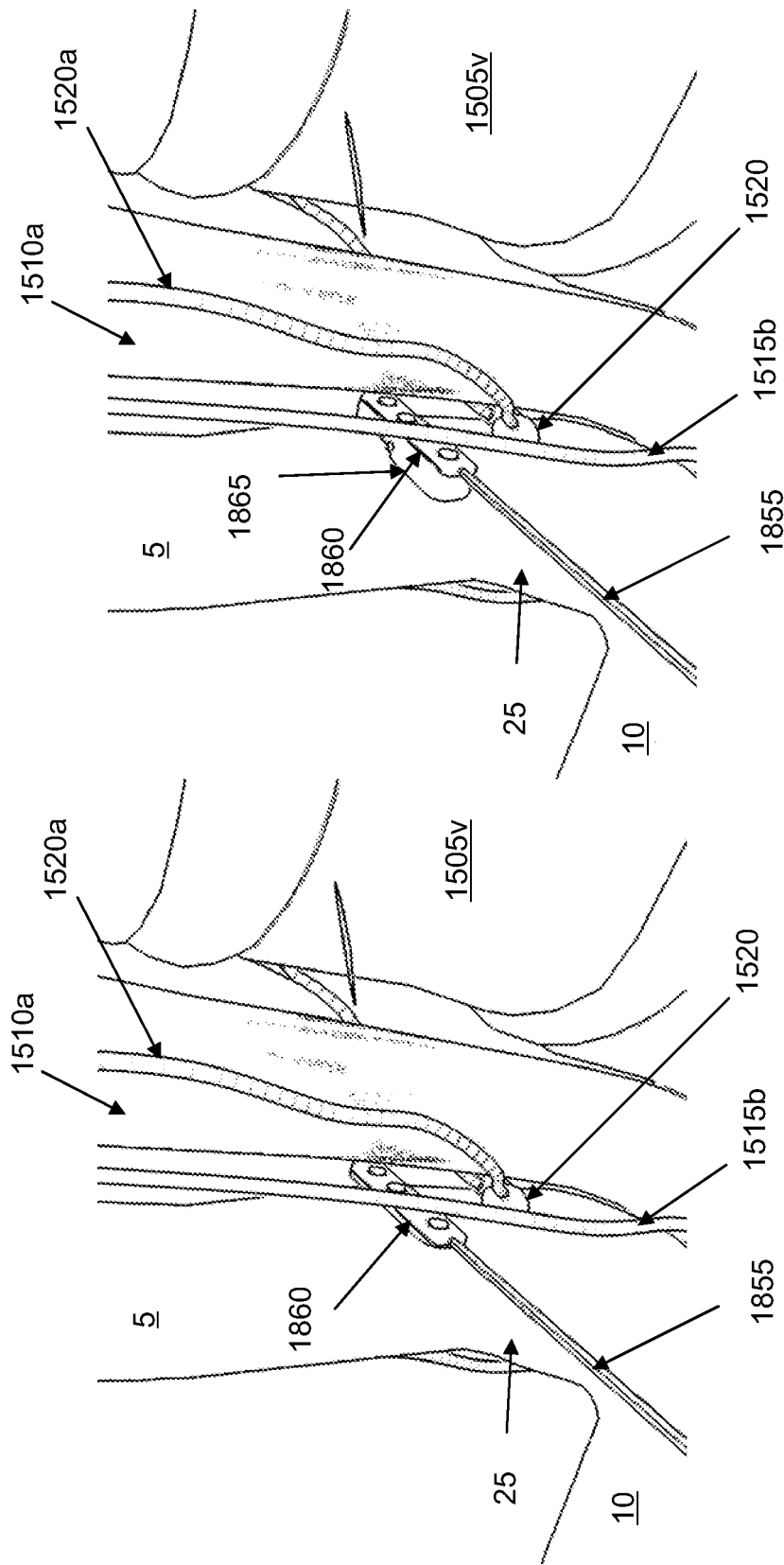

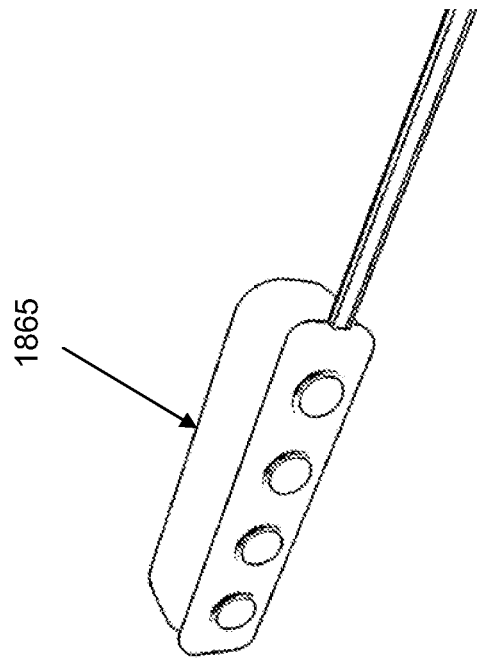
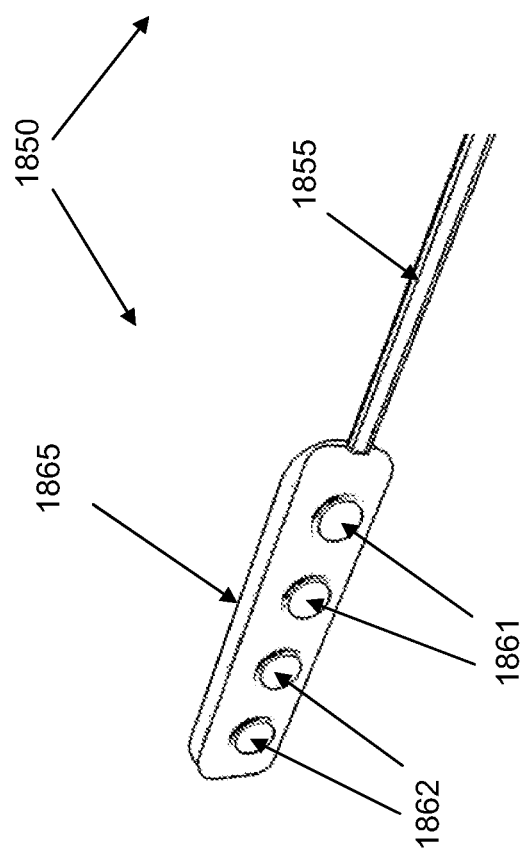
FIG. 19B
FIG. 19A

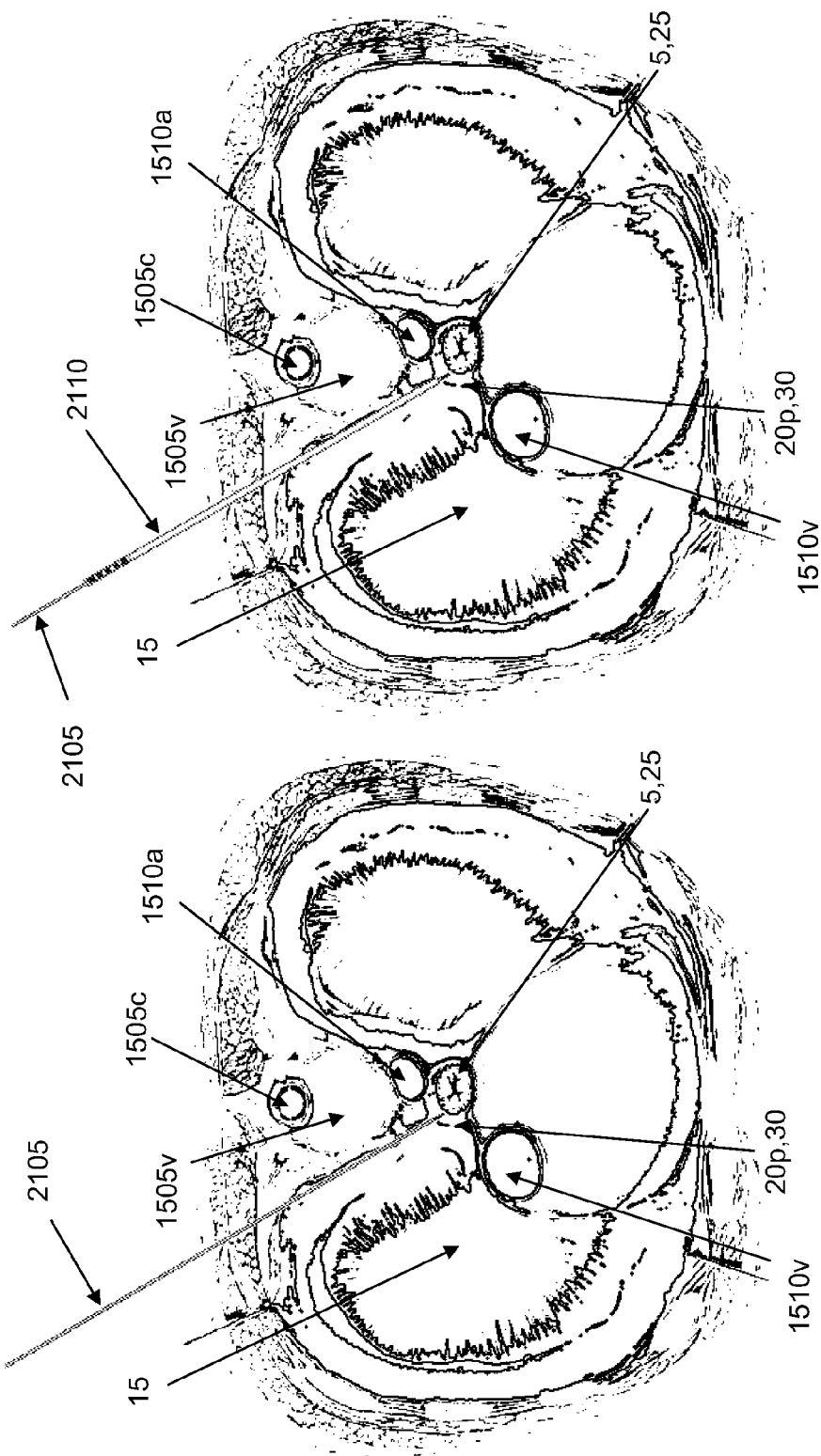

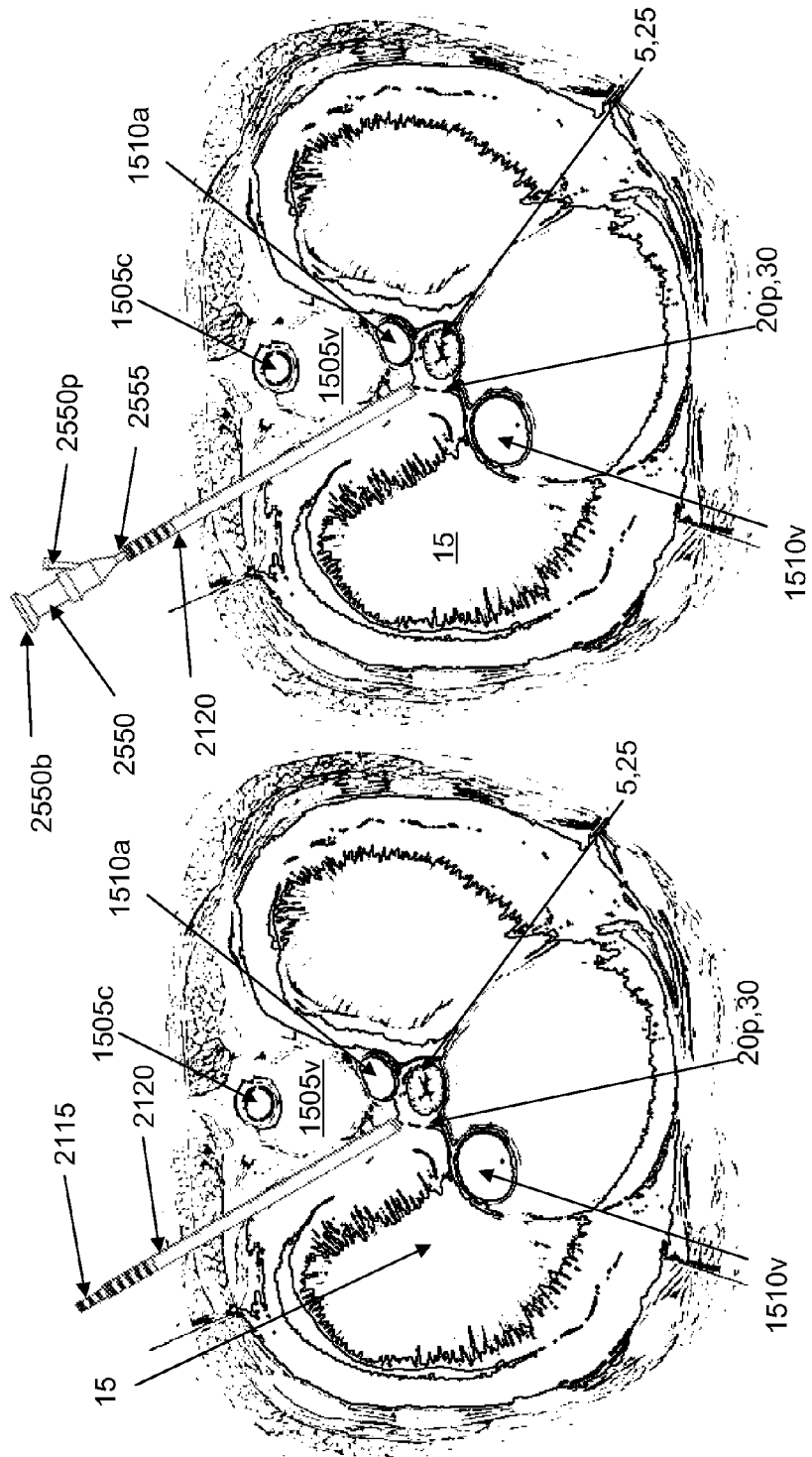

APPARATUS AND METHODS FOR MINIMALLY INVASIVE OBESITY TREATMENT

CROSS-REFERENCE TO OTHER APPLICATIONS

This application is a national stage of International Application No. PCT/US2009/050429, filed Jul. 13, 2009, which claims priority to U.S. Provisional No. 61/080,175, filed Jul. 11, 2008 and U.S. Provisional No. 61/134,827, filed Jul. 14, 2008.

BACKGROUND OF THE INVENTION

1. Field of the Invention

The present invention generally relates to apparatus and methods for minimally invasive treatment of obesity.

2. Description of the Related Art

Obesity is a major health concern in many countries and is particularly prevalent in developed countries. Almost one-third of the adult American population is considered to be obese, while almost two-thirds of adult Americans are categorized as being obese or overweight. The number of overweight and obese Americans has continued to increase since 1960. Obesity is now an increasingly common health concern that affects many teenagers and children as well as adults.

Obesity is also a risk factor for a broad range of diseases and conditions, including diabetes, coronary artery disease, sleep apnea, gastro-esophageal reflux disease (GERD), and cancer of the breast, prostate and colon. As a result, obesity adds enormously to the costs of healthcare in the U.S.

Each year, obesity causes at least 300,000 excess deaths in the U.S., and healthcare costs of American adults with obesity amount to approximately $100 billion. Furthermore, obese individuals may become victims of discrimination in employment and social settings leading to inferior lifestyle, lower socio-economic status, and possible psychological and mental health problems.

Treatment regimes for obesity have included various diets, exercise programs, and lifestyle counseling, as well as pharmaceutical compositions and surgery. Numerous surgical procedures for the treatment of obesity are known in the prior art. One surgical approach to obesity treatment is gastric bypass surgery, which leads to decreased nutrient absorption by the patient. Another approach to the treatment of obesity is the insertion of an intra-gastric balloon to mimic fullness of the stomach. A further approach is the application of a band around the stomach wall to restrict gastric volume. Yet another approach is the insertion of an intraluminal filter or valve at the gastro-esophageal junction to restrict passage of food into the stomach. Still another approach is the direct electrical stimulation of the stomach wall to decrease the normal peristaltic motility of the stomach.

The procedures outlined above have generally been of limited value, and in addition have various disadvantages. For example, insertion of an intra-gastric balloon in the stomach is invasive and may have serious side effects, e.g., by interfering with the digestion of food. Similarly, various gastric bypass procedures, in which a portion of the gastro-intestinal tract is surgically excised, have led to under-nourished or malnourished patients, and furthermore such procedures are typically highly invasive and irreversible.

As can be seen, there is a need for apparatus, systems, and methods for the safe, reliable, cost-effective, and minimally invasive treatment of obesity.

SUMMARY OF THE INVENTION

The present invention provides apparatuses and methods for the effective and minimally invasive treatment of obesity. In one embodiment, a method for treating a patient, includes: introducing an electrode at least partially into a gastroesophageal (GE) space formed between an inner wall of a phrenoesophageal ligament (POL) and outer walls of the esophagus and cardiac orifice; and modulating tissue using the electrode.

In one aspect of the embodiment, the electrode is introduced substantially or wholly within the GE space. In another aspect, the method further includes securing the electrode to the POL. The electrode may be secured to an interior or exterior portion of the POL. In another aspect, the method further includes promoting a feeling of satiety in the patient during or after modulation. In another aspect, the tissue includes a portion of the diaphragm. The tissue may further include a portion of the nerve that innervates the diaphragm portion. In another aspect, the tissue includes a portion of a vagal nerve. In another aspect, the tissue includes a portion of a splanchnic nerve. In another aspect, the tissue includes a portion of a celiac ganglion. A ventral aspect of the diaphragm portion, vagal nerve, or celiac ganglion may be modulated.

In another aspect, the method further includes modulating tissue using the electrode provides a signal from the electrode towards an aspect of a neural structure that faces towards a portion of the POL used to support the electrode. The method may further include advancing the electrode within the GE space into a position adjacent a ventral aspect of a portion of the tissue. The method may further include passing a least a portion of the electrode out of the GE space towards a portion of the tissue. The method may further include passing at least a portion of the electrode in a dorsal direction out of the GE space towards a portion of the tissue. The method may further include passing at least a portion of the electrode out of the GE space towards a portion of the tissue without passing the electrode beyond a coronal plane passing though a portion of the aorta. The portion of the aorta may include a ventral aspect of the aorta. The portion of the aorta may include a dorsal aspect of the aorta.

In another aspect, the method further includes forming an opening in the POL, and thereafter introducing the electrode into the GE space through the opening. The method may further include laterally inserting a surgical instrument into the patient before forming the opening. The method may further include anteriorly inserting a surgical instrument into the patient before forming the opening. The electrode may be introduced endoscopically through a trocar. The method may further include posteriorly inserting a surgical instrument into the patient and thereafter forming the opening in the GE space. The instrument may include a guide wire and one or more dilators. In another aspect, the electrode is mounted on a paddle. In another aspect, the electrode is mounted on a steerable catheter. In another aspect, the electrode is introduced using an endoscope.

In another embodiment, a method for treating a patient, includes: approaching a portion of the phrenoesophageal ligament (POL) with an instrument; advancing an electrode along the instrument to a position adjacent the POL; and applying a electrical signal to tissue adjacent to the POL using the electrode. In one aspect of the embodiment, the method further includes supporting at least a portion of the electrode with the POL. At least a portion of the electrode may be adjacent to an outer or inner layer of the POL. In another aspect, the approaching step further includes advancing the instrument dorsally towards the POL. In another aspect, the approaching step further includes advancing the instrument ventrally towards the POL. In another aspect, the approaching step further includes advancing the instrument laterally towards the POL.

In another aspect, the POL portion is superior to the diaphragm. The POL portion may be lateral of a spinal midline. In another aspect, the POL portion is inferior to the diaphragm. The POL portion may be lateral of a spinal midline. In another aspect, applying a signal includes applying a signal that modulates neural activity. In another aspect, applying a signal includes applying a signal that inhibits neural activity. In another aspect, applying a signal includes applying a signal that stimulates neural activity. In another aspect, the tissue adjacent to the POL includes a neural tissue. In another aspect, the neural tissue includes at least one of: a portion of a vagal nerve; a portion of splanchnic nerve; a portion of a celiac ganglion or a portion of a nerve that innervates a portion of a diaphragm. In another aspect, the tissue adjacent to the POL includes muscle tissue. In another aspect, the muscle tissue includes a diaphragm. In another aspect, the muscle includes a stomach.

In another embodiment, a method for treating a patient, includes: forming an opening in the phrenoesophageal ligament (POL); introducing a balloon through the opening and into a gastroesophageal (GE) space formed between an inner wall of the POL and outer walls of the esophagus and cardiac orifice; and inflating the balloon to provide therapy to the patient. In one aspect of the embodiment, the therapy includes at least partially restricting the esophagus and/or cardiac orifice in proximity to the balloon. In another aspect, the therapy includes: urging an electrode disposed at least partially within the GE space into closer proximity to a targeted neural structure and thereafter delivering an electrical signal to the targeted neural structure with the electrode. In another aspect, at least a portion of the balloon is disposed between diaphragm and the cardiac orifice and/or esophagus. Inflating the balloon may distend at least a portion of the diaphragm. Inflating the balloon may distend at least a portion of the cardiac orifice. Inflating the balloon may distend at least a portion of the esophagus. In another aspect, after inflating the balloon, at least a portion of the balloon is generally shaped like an ellipsoid, an egg, a cylinder, or a polyhedron.

In another aspect, the opening is formed by: advancing a surgical instrument towards the POL; and engaging the POL with the distal end of the instrument. The POL may be engaged by grasping the POL with the instrument. The POL may be further engaged by separating the POL from tissue within the GE space. The POL may be separated before forming the opening. The POL may be engaged by applying a vacuum to the POL using the instrument. The POL may be engaged by advancing tines from the distal end of the surgical instrument and piercing the POL. In another aspect, the method further includes fastening the balloon to the POL.

In another aspect, the balloon includes a first wall having a first stiffness, a second wall having a second stiffness, and a partition, the first wall and the partition enclose a first chamber, the second wall and the partition enclose a second chamber, and the second stiffness is greater than the first stiffness. The first wall may exert pressure on the wall of the cardiac orifice and/or esophagus, and the second wall may be supported by the diaphragm. The first chamber may be in fluid communication with a first valve, the second chamber may be in fluid communication with a second valve, and the valves may provide for independent inflation of the chambers. In another aspect, the balloon is inflated to a first size, and the method further includes inflating the balloon to a second larger size after a period of time sufficient for the patient to become accustomed to the balloon.

In another aspect, the balloon is inflated until a balloon pressure reaches a predetermined pressure. In another aspect, the method further includes: inserting a pressure sensor into the esophagus and/or cardiac orifice to a position adjacent the balloon; and monitoring pressure of the balloon using the pressure sensor while inflating the balloon. Inflating the balloon may be performed until a predetermined pressure is measured by the pressure sensor that corresponds to a desired degree of luminal restriction. In another aspect, the therapy includes inflating the balloon to provide a degree of luminal restriction. The degree of luminal restriction may be provided in at least a portion of the esophagus. The degree of luminal restriction may be provided in at least a portion of the stomach.

In another aspect, the balloon is inflated to a first size, and the method further includes: injecting a contrasting agent into the esophagus and cardiac orifice; imaging at least a portion of the esophagus and the cardiac orifice; determining a diameter of the restriction of the esophagus and/or cardiac orifice using the image. In another aspect, the balloon further exerts pressure on the stomach fundus. In another aspect, the method further includes: inserting a trocar into a thorax or abdomen of the patient; and inserting a working catheter into the trocar, wherein: the working catheter includes the balloon connected to a balloon catheter, and the balloon is inflated by injecting fluid into the balloon catheter. The working catheter may further include an endoscope. In another aspect, the esophagus and/or cardiac orifice lumen is restricted to a first diameter, thereby restricting a rate of food intake by the patient. In another aspect, the esophagus and/or cardiac orifice lumen is restricted to a first diameter, thereby facilitating esophageal closure. In another aspect, the esophagus and/or cardiac orifice lumen is restricted to a first diameter, thereby inhibiting or restricting reflux of stomach contents into the esophagus.

In another aspect, the method further includes modulating tissue using an electrode attached to the balloon. The tissue may include diaphragmatic muscle. The tissue may include a vagal nerve. The tissue may further include a splanchnic nerve and/or a celiac ganglion. At least two pairs of electrodes may be attached to the balloon and inflating the balloon may press a first pair against a vagal nerve and a second pair of the electrodes against a splanchnic nerve and/or a celiac ganglion. In another aspect, the method further includes: performing the inflating step until an electrode moves into closer proximity to a portion of a vagal nerve; a portion of a splanchnic nerve; a portion of a celiac ganglion or a portion of a nerve that innervates a portion of a diaphragm. The portion of the vagal nerve may include a ventral aspect of the vagal nerve; the portion of the splanchnic nerve may include a ventral aspect of the splanchnic nerve; or the portion of a celiac ganglion may include a ventral aspect of the celiac ganglion.

In another embodiment, a catheter assembly for insertion into a patient, includes: a working catheter; a balloon catheter disposed in the working catheter; and a balloon connected to the balloon catheter, inflatable by injection of fluid through the balloon catheter, and including a first wall having a first stiffness, a second wall having a second stiffness, and a partition, wherein the first wall and the partition enclose a first chamber and the second wall and the partition enclose a second chamber. In one aspect of the embodiment, at least a portion of an inflated shape of the balloon is an ellipsoid, an egg, a cylinder, or a polyhedron. In another aspect, the second stiffness is greater than the first stiffness. In another aspect, the second stiffness is substantially greater than the first stiffness. In another aspect, the balloon catheter includes a first lumen in fluid communication with the first chamber and a second lumen in fluid communication with the second chamber.

In another aspect, the assembly further includes: a first valve is in fluid communication with the first chamber; and a second valve is in fluid communication with the second chamber, wherein operation of the valves provides independent fluid communication with the chambers. In another aspect, the balloon is made from or coated with a biocompatible material. In another aspect, the assembly further includes a wire preformed into a hook, wherein the wire is operable between: a first position where the wire is elastically restrained inside the working catheter, and a second position where the wire returns to the preformed hook as the wire is extended from the working catheter. In another aspect, the assembly further includes an inner catheter disposed between the hook and the balloon catheter. In another aspect, the assembly further includes an electrode attached to an outer surface of the balloon. In another aspect, the assembly further includes: an adapter connecting the balloon catheter and the balloon; and a lug extending from an outer surface of the adapter.

In another embodiment, a device for providing therapy to a patient, includes: an inflatable structure adapted and configured for positioning at least partially within a gastroesophageal (GE) space formed between an inner wall of a phrenoesophageal ligament (POL) and outer walls of the esophagus and cardiac orifice; and an electrode structure adapted and configured for positioning at least partially within the GE space. In one aspect of the embodiment, when the inflatable structure is inflated at least a portion of the inflatable structure is shaped like an ellipsoid, an ovoid, a cylinder, a polyhedron or a portion of a curve. In another aspect, the electrode structure comprises flexible base that is sufficiently flexible to follow at least a portion of the interior shape of the GE space. In another aspect, at least a portion of the electrode structure is attached to the inflatable structure.

In another aspect, the inflatable structure has a length selected to be less than the perimeter of the esophageal wall within the GE space. In another aspect, the inflatable structure has a length selected such that in use within the GE space, the inflatable structure circumscribes less than half the perimeter of the esophageal wall within the gastroesophageal (GE) space. In another aspect, the electrode structure has a length selected to be less than the perimeter of the esophageal wall within the GE space. In another aspect, the electrode structure has a length selected such that in use within the GE space, the electrode structure circumscribes less than half the perimeter of the esophageal wall within the GE space. In another aspect, the respective sizes of the electrode structure and the inflatable structure are selected such that both structures may be within the GE space without contacting one another. In another aspect, the electrode structure has a length selected such that in use within the GE space, the electrode structure circumscribes a first portion of the perimeter of the esophageal wall within the GE space and the inflatable structure has a length selected such that in use within the GE space the inflatable structure circumscribes a second portion of the perimeter of the esophageal wall within the GE space without overlapping with the first portion.

In another embodiment, a method of treating a patient, includes: positioning an electrode at or near a portion of the phrenoesophageal ligament (POL); advancing the electrode towards a neural target in proximity to the POL; and applying an electrical signal to the neural target using the electrode. In one aspect of the embodiment, advancing the electrode includes advancing the electrode towards a ventral aspect of the neural target. In another aspect, advancing the electrode includes advancing the electrode towards the neural target without passing through a coronal plane passing through a portion of the aorta. The coronal plane may pass through a portion of the aorta passes through a ventral aspect of the aorta. The coronal plane may pass through a portion of the aorta passes through a dorsal aspect of the aorta.

In another aspect, the neural target comprises at least a portion of a vagal nerve, a splanchnic nerve, a celiac ganglion or a nerve that innervates a portion of a diaphragm. In another aspect, after positioning the electrode at or near a portion of the POL, at least a portion of the electrode is positioned at least partially within a gastroesophageal (GE) space formed between an inner wall of the POL and an outer wall of the esophagus and an outer wall of the stomach. In another aspect, advancing the electrode includes advancing the electrode towards the neural target without passing through a coronal plane positioned at a ventral aspect of a vertebral body adjacent the POL. In another aspect, advancing the electrode towards a neural target in proximity to the POL further includes: advancing the electrode in a lateral direction away from a portion of the POL. In another aspect, advancing the electrode towards a neural target in proximity to the POL further includes: advancing the electrode in a dorsal direction away from a portion of the POL. In another aspect, advancing the electrode towards a neural target in proximity to the POL further includes: advancing the electrode in a cephalad direction away from a portion of the POL. In another aspect, advancing the electrode towards a neural target in proximity to the POL further includes: advancing the electrode in a caudal direction away from a portion of the POL.

BRIEF DESCRIPTION OF THE DRAWINGS

FIGS. 4-8 illustrate acts of a method for implanting the balloon, according to another embodiment of the present invention. FIGS. 4A and 4B illustrates locations of trocars for catheter insertion. FIG. 5 illustrates placement of the working catheter. FIGS. 6A-C illustrate deployment of hooks from the working catheter. FIGS. 7A-C illustrate engagement and tearing of the POL for insertion of the balloon. FIGS. 8A and 8B illustrate insertion of the balloon into the POL opening and inflation of the balloon against the cardiac orifice/esophageal wall.

FIGS. 9A-9D illustrate an optional additional anchor for retaining the balloon in the GE space.

FIGS. 10A-11C illustrate a bi-chamber balloon, according to another embodiment of the present invention.

FIGS. 13A-13D illustrate a method for determining the diameter of the cardiac orifice/esophagus at different inflation levels of the balloon using a barium swallow.

FIGS. 15A, 15C, and 15D illustrate a method for implanting an electrode 1560 for treating obesity, according to another embodiment of the present invention. FIG. 15B illustrates an alternate approach.

FIGS. 16A and 16B illustrate a neuromodulator.

FIGS. 18A and 18B illustrate implanting a balloon electrode, according to another embodiment of the present invention.

FIGS. 19A and 19B illustrate the electrode assembly in deflated and inflated positions, respectively.

FIGS. 21A-H illustrate an alternative method for implanting the balloon electrode, according to another embodiment of the present invention.

FIGS. 25A and 25B illustrate posterior endoscopic implantation of the catheter electrode, according to another embodiment of the present invention.

DETAILED DESCRIPTION OF THE INVENTION

The detailed description that follows is not to be taken in a limiting sense, but is made primarily for the purpose of illustrating the general principles of the various aspects of the present invention. The scope of the invention is best defined by the claims appended hereto.

Figure 1:
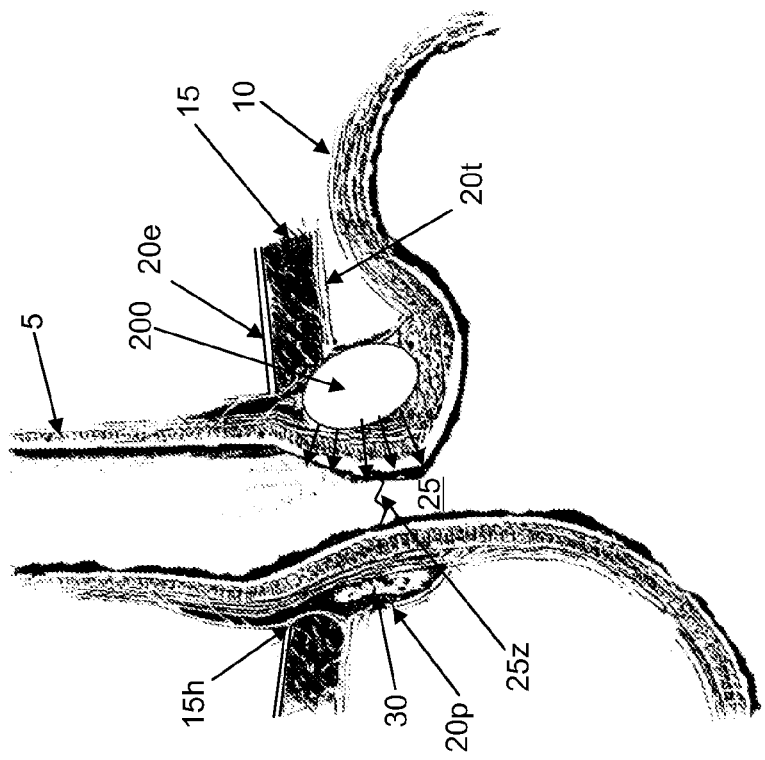
FIG. 1 is a view of a portion of a human gastro-intestinal (GI) tract.

FIG. 1 is a view of a portion of a human gastro-intestinal (GI) tract. FIG. 1A is a cross section of the GI tract. The GI tract includes the esophagus 5, the stomach 10, the diaphragm 15, and the cardiac orifice 25. The histology change between esophageal tissue and gastric tissue occurs at the z-line 25z. The esophagus 5 passes through an opening 15h of the diaphragm 15, known as the esophageal hiatus 15h. Proximately above the hiatus 15h, the esophagus 5 is anchored to the diaphragm 15 by an upper limb of the phrenoesophageal ligament (POL) 20p. The POL 20p is formed from two closely applied layers including a layer derived from endothoracic fascia 20e and a layer derived from transversalis fascia 20t. A lower limb of the POL 20p attaches to the stomach 10 proximately below the hiatus 15h. A gastroesophageal (GE) space 30 is formed between an inner wall of the POL 20p and outer walls of the esophagus 5 and cardiac orifice 25. The gastroesophageal (GE) space 30 is filled with adipose tissue and traversed by blood vessels.

Figure 2:
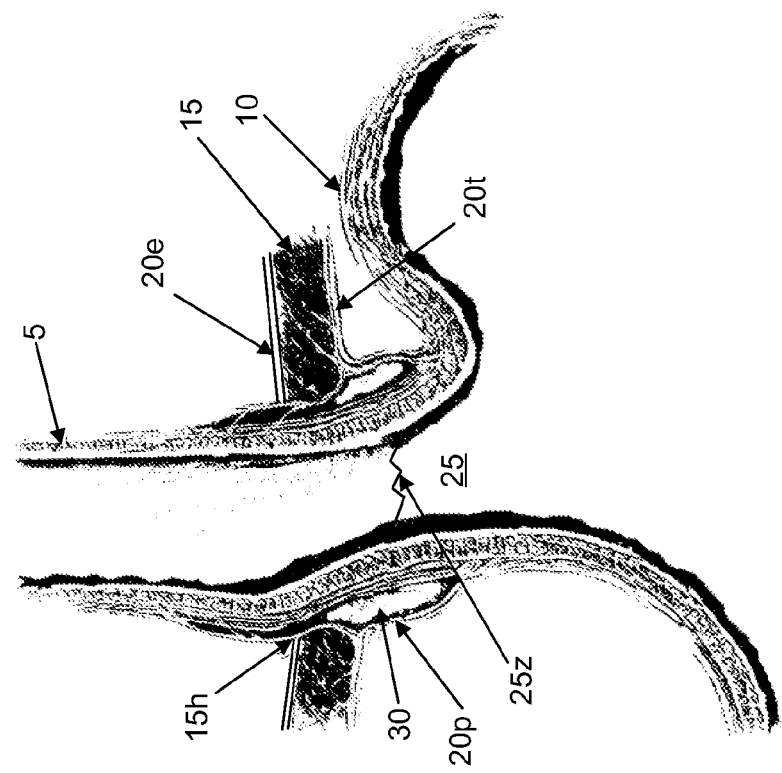
FIG. 2 is a view of the GI tract portion where the cardiac orifice and/or esophagus are being restricted by a balloon, according to one embodiment of the present invention.
Figures 1A, 2A:
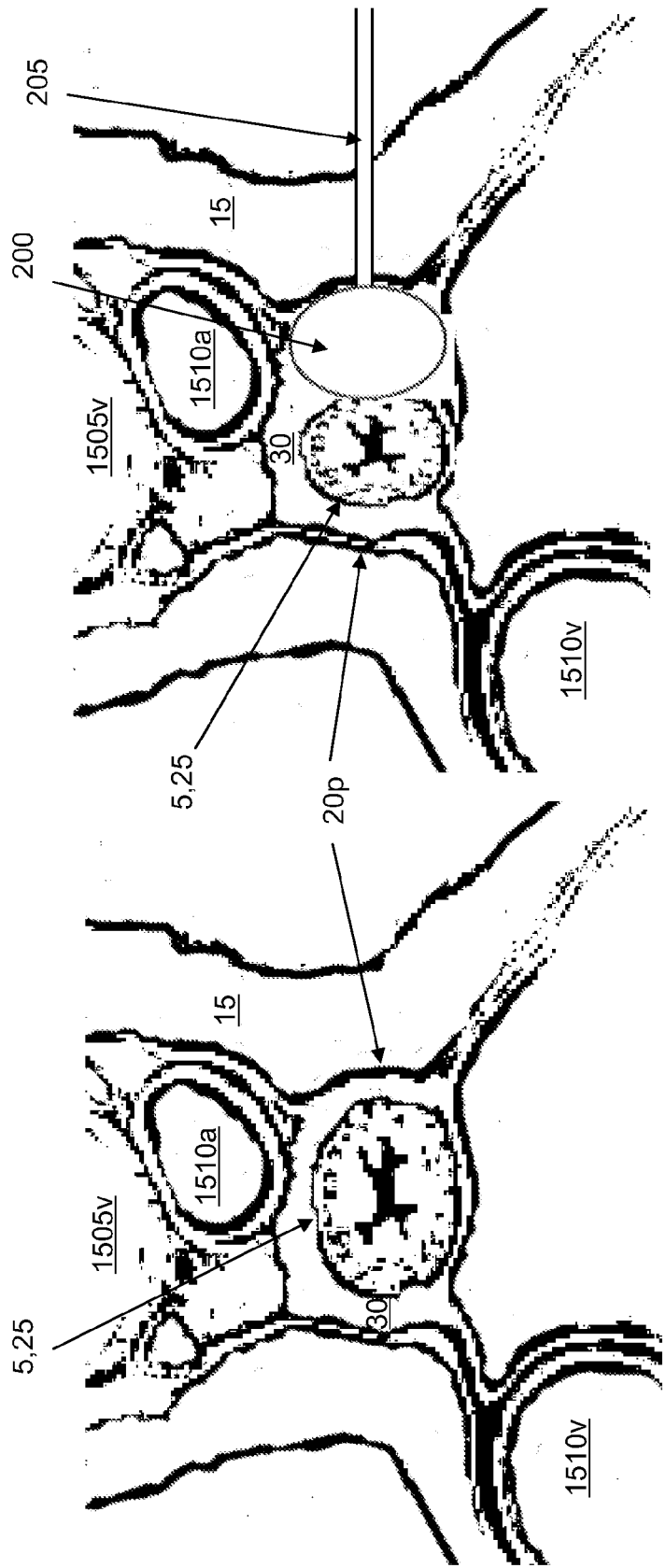
FIG. 1A is a cross section of the cardiac orifice/esophagus.
FIG. 2A is a cross section of the restricted cardiac orifice/esophagus.

FIG. 2 is a view of the GI tract portion where the cardiac orifice 25 and/or esophagus 5 are being restricted by an inflatable member, such as a balloon 200, according to one embodiment of the present invention. FIG. 2A is a cross section of the restricted cardiac orifice/esophagus 25,5. The balloon 200 has been implanted sub-fascially within the GE space 30 at the cardiac orifice/esophagus 25,5 proximate to the diaphragm 15. The balloon 200 has been implanted proximately below the diaphragm, but an end of the balloon 200 extends between the cardiac orifice/esophagus wall and the diaphragm 15 into the hiatus 15h to retain the balloon in place. Alternatively, the balloon 200 may be implanted anywhere along the GE space 30, such as at the diaphragm 15 or proximately above the diaphragm. The balloon 200 has been inflated by injecting an inflation fluid into the balloon 200. The inflation fluid may be a liquid, such as physiological saline or other aqueous liquids, a gel, a gas, a polymer, a biocompatible material, or any suitable filling material and combinations thereof. The balloon 200 may include a wall made from an extensible material enclosing a chamber. The material may be a biocompatible material or the wall may be coated with a biocompatible material. The extensible material may be a polymer, such as an elastomer or a thermoplastic. When inflated, the shape of the balloon 200 may be an ellipsoid (i.e., a prolate), an egg, a cylinder, a polyhedron (i.e., rectangular prism) or any suitable shape. The balloon 200 may also have a contour or wedged portion to conform to the esophagus/cardiac orifice 5,25.

The wall may have a port formed therethrough for connection to a balloon catheter 205. The balloon catheter 205 may be connected to a syringe or pump for injection of the inflation fluid into the balloon chamber. Inflation of the balloon 200 exerts pressure on a portion of the cardiac orifice/esophagus wall, thereby restricting the cardiac orifice/esophagus lumen. Restriction of the cardiac orifice/esophagus lumen may be accomplished without surrounding the cardiac orifice/esophagus because of a reactionary pressure or force exerted on a face of the balloon distal from the cardiac orifice/esophagus by the diaphragm 15 and/or a reactionary pressure or force exerted on the cardiac orifice/esophagus wall by the diaphragm 15. In one embodiment, the inflated balloon is in contact with less than an entire circumference of the cardiac orifice/esophagus, preferably, less than half of the circumference. Without being bound by theory, it is believed that restriction of the cardiac orifice/esophagus lumen may reduce the rate at which the patient can consume food, thereby giving the patient's stomach more time to signal the patient's brain that the patient has consumed enough food. Restriction of the cardiac orifice/esophagus lumen may further require the patient to chew food more thoroughly and consume more fluids with meals, thereby further reducing the patient's caloric intake. As such, the balloon 200 is useful for treating obesity. Restriction of the cardiac orifice/esophagus lumen may also prevent or inhibit reflux of stomach contents into the esophagus, thereby preventing or treating gastro-esophageal reflux disease (GERD).

Figures 3A, 3B:
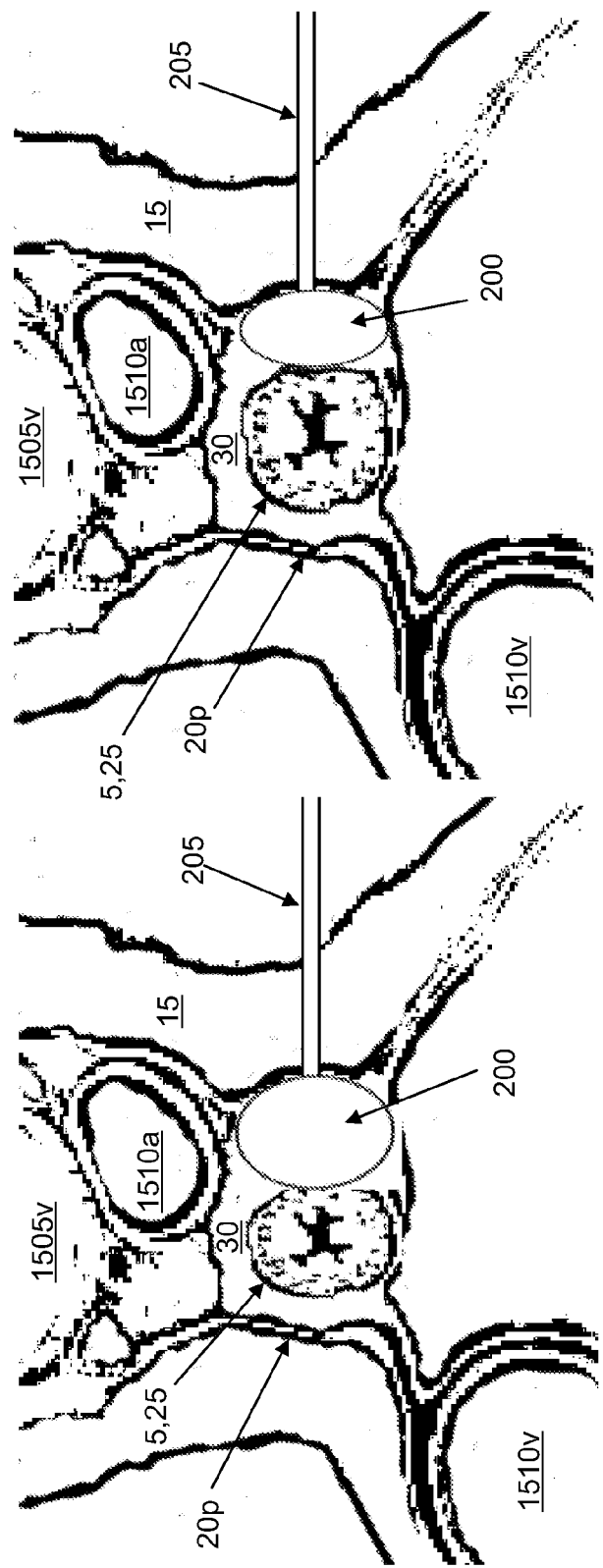
FIG. 3A is a cross section of the balloon inflated to a first size.
FIG. 3B is a cross section of the balloon inflated to a smaller second size.

FIG. 3A is a cross section of the balloon 200 inflated to a first size. FIG. 3B is a cross section of the balloon 200 inflated to a smaller second size. The balloon catheter 205 may remain in the patient after implantation of the balloon 200 so that inflation of the balloon may be adjusted post-implantation. For example, the balloon 200 may be inflated to the second smaller size after initial implantation. The patient may then become accustomed to the smaller size for a period of time, such as one week to a few months before the size of the balloon is further increased to the first larger size. Further, the optimal size of the balloon 200 may vary according to an individual patient so that the optimal size may have to be determined iteratively.

FIGS. 4-8 illustrate acts of a method for implanting the balloon 200, according to another embodiment of the present invention. FIGS. 4A and 4B illustrates locations of one or more trocars 405, 410 for catheter insertion. The trocars 405, 410 may be located in the abdomen. Alternatively, the trocars 405, 410 may be located in the thorax, especially for the alternative where the balloon is implanted above the diaphragm. A first trocar 405 may be inserted for providing a channel for an endoscope (not shown) and a second trocar 410 may be inserted for providing a channel for a working catheter 500. Alternatively, the working catheter 500 may incorporate the endoscope or the endoscope may be omitted so that only one trocar 405 is required.

FIG. 5 illustrates placement of the working catheter 500. The catheter 500 may be inserted until a distal end is located between the stomach 10 and the diaphragm 15 proximate to the POL 20p. Alternatively, as discussed above, the balloon 200 may be located above the diaphragm 15. In this alternative, the catheter 500 may be located proximately above the diaphragm.

FIGS. 6A-C illustrate deployment of hooks 505 from the working catheter 500. FIGS. 7A-C illustrate engagement and tearing of the POL 20p for insertion of the balloon 200. The working catheter 500 may include an outer wall, one or more gripping devices such as hooks 505, an inner catheter 510, and the balloon catheter 205. The outer wall may be made from a rigid material, such as a polymer, such as a thermoset or thermoplastic, such as polyvinylchloride (PVC). The balloon catheter 205 may be disposed in the inner catheter lumen 515. The hooks 505, inner catheter 510, and balloon catheter 205 may be concentrically or eccentrically arranged within the working catheter 500. Alternatively, as discussed above, the working catheter 500 may also include the endoscope. The inner catheter 510 may serve to protect the balloon catheter from the hooks.

The hooks 505 may be connected to a sleeve (not shown) extending through the working catheter 500 so that the hooks may be manually operated from outside the patient. The hooks 505 may be made from a ductile material, such as a metal or alloy, such as stainless steel or titanium. The hooks 505 may also be made from wire and have distal ends that taper to a sharp point. In one embodiment, the hooks are made from a shape memory metal or alloy. An end portion of each hook 505 may be plastically deformed into a curved shape so that when the hooks are extended from the working catheter, the end portions return to the curved shape and grasp the POL 20p. The POL 20p may then be separated from the GE space tissue by pulling and/or rotating the working catheter 500. Once an opening in the POL 20p is formed, the hooks 505 may be withdrawn back into the working catheter 500 or sleeve, thereby elastically returning them to a straight or substantially straight position.

FIGS. 8A and 8B illustrate insertion of the balloon 200 into the POL opening and inflation of the balloon against the cardiac orifice/esophageal wall. The balloon 200 and a distal portion of the balloon catheter 205 are pushed through and exit the working catheter 500 into the POL opening. A syringe or pump connected to a proximate end of the balloon catheter 205 is operated to inflate the balloon 200, thereby restricting the cardiac orifice/esophagus lumen. The working catheter 500 may then be withdrawn from the patient. A portion of the balloon catheter 205 may be left in the patient for adjusting inflation of the balloon, as discussed above. Depending on the size, shape, and placement of the balloon, inflation of the balloon may be sufficient to retain the balloon 200 into place.

FIGS. 9A-9D illustrate an optional additional anchor for retaining the balloon 200 in the GE space 30. An adapter 205 may connect the balloon 200 to the balloon catheter 205. One or more lugs 215 may extend from an outer surface of the adapter 205. Each lug 215 may be engaged by a respective hook 220. The hooks 200 may be made from one of the materials discussed above with respect to the hooks 505. The hooks 220 may be plastically formed into a coil shape and elastically restrained into a hook shape so that when the working catheter 500 is removed, the hooks are released and return to the coil shape, thereby anchoring the adapter and the balloon to the POL. Alternatively, the hooks 220 may be subsequently crimped into a coil. Alternatively, the adapter may be sutured or stapled to the fascia instead of using the hooks.

FIGS. 10A-11C illustrate a bi-chamber balloon 1000, according to another embodiment of the present invention. The bi-chamber balloon 1000 may include a first wall 1005, a second wall 1010, a partition 1015, a catheter 1030, and an adapter 1035. The walls 1005, 1010 enclose a chamber. The walls 1005, 1010 may be made from an extensible material enclosing a chamber. The material may be a biocompatible material or the wall may be coated with a biocompatible material. The extensible material may be a polymer, such as an elastomer or a thermoplastic. When inflated, the shape of the balloon may be an ellipsoid (i.e., a prolate), an egg, a cylinder, a polyhedron (i.e., rectangular prism) or any suitable shape. Alternatively, the balloon 1000 may have any suitable number of chambers including three or more chambers.

The partition 1015 divides the chamber into a first chamber 1005a and a second chamber 1010a. The first wall 1005 has a first stiffness and the second wall 1010 and has a second stiffness. The first stiffness may be less than or substantially less than the second stiffness. The different stiffness may be accomplished by using different materials, different thickness, materials with different durometers, or combinations thereof. For example, the first wall 1005 may be made from an elastomer having a low amount of cross-linking and the second wall 1010 may be made from an elastomer having a higher amount of cross-linking. In another example, the first wall 1005 may be made from an elastomer and the second wall 1010 may be made from a thermoplastic. The partition 1015 may be a composite of the first and second walls bonded together (each wall is a separate balloon) or may be made from only one of the first and second materials. In another embodiment, the bi-chamber balloon 1000 may be formed by adjoining two single chamber balloons.

The balloon 1000 may be oriented so that the first wall 1005 faces the cardiac orifice/esophagus and the second wall faces the diaphragm 15 and/or stomach 10. Placement of the balloon 1000 in this manner encourages the first wall 1005 to expand toward the cardiac orifice/esophagus and discourages the first wall from expanding toward the more rigid second wall. The second wall may further be supported by the POL 20p, the stomach 10, and/or the diaphragm 15. The stiffness of the second wall 1010 may further be selected so that it is greater or substantially greater than the stiffness of the cardiac orifice/esophagus.

The balloon catheter 1025 may include a first lumen for the first chamber and a second lumen for the second chamber. The lumens may be arranged concentrically or eccentrically. The adapter 1035 connects the balloon catheter 1025 to the second wall 1010 and provides fluid communication between the second lumen and the second chamber. The catheter 1030 is connected to the adapter 1025 and a port formed through the partition 1015 and provides fluid communication between the first lumen and the first chamber. A valve manifold 1050 connects to a proximate end of the balloon catheter and also connects to a pump or syringe. The valve manifold may be coupled to the balloon catheter using an injection port. The injection port may be positioned outside a patient's body or inside the skin to facilitate attachment of the valve manifold 105. The valve manifold includes a first valve having a first button 1055 and a second valve having a second button 1060. Actuation of the first button provides fluid communication between the pump or syringe and the first chamber and actuation of the second button 1060 provides fluid communication between the second chamber and the pump or syringe. The valves may be biased so that non-actuation of a respective button closes the respective valve. FIGS. 11A and 11C illustrate different inflation sizes of the first chamber while the inflation size of the second chamber is constant. The bi-chamber balloon 1000 may be used with any of the methods, discussed above, for the balloon 200.

Figure 12A:
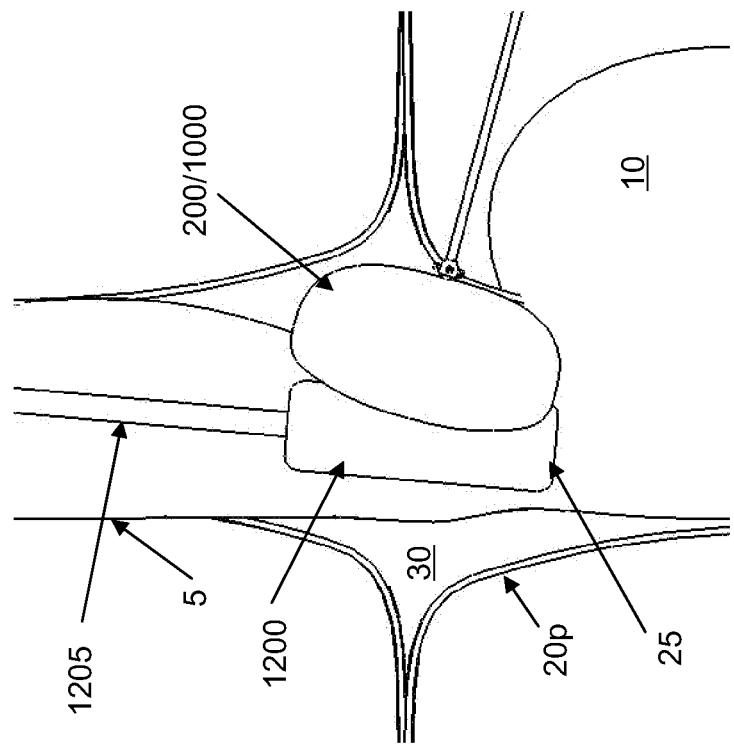
FIGS. 12A and 12B illustrate a method for measuring pressure exerted on the esophagus/cardiac orifice by different inflation levels of the balloon.
Figure 12B:
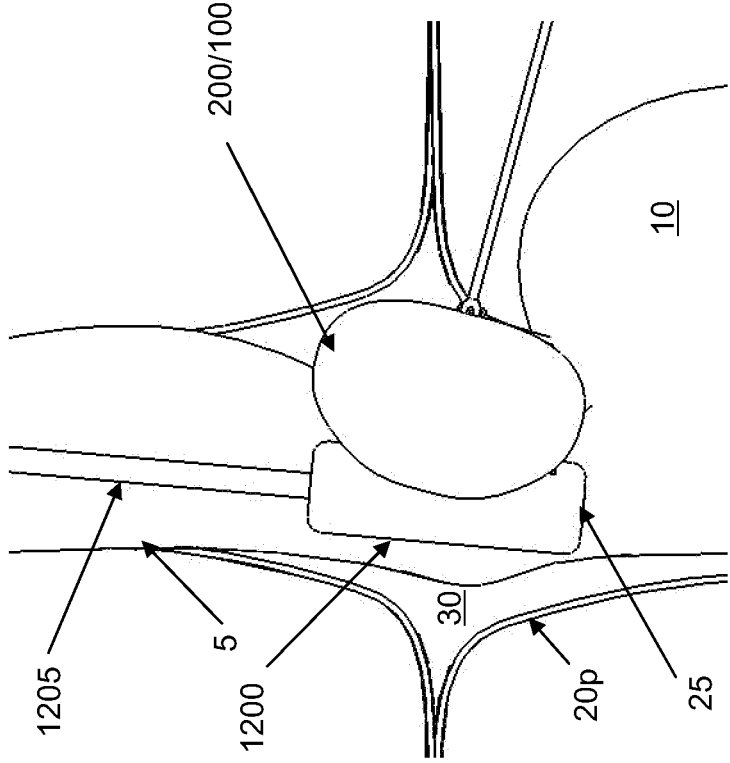

FIGS. 12A and 12B illustrate a method for measuring pressure exerted on the cardiac orifice/esophagus by different inflation levels of the balloon 200/1000. A pressure sensor 1200 connected to a catheter 1205 is inserted down the patient's throat until the pressure sensor is in alignment with the balloon. The catheter includes wires providing electrical and data communication between the pressure sensor and a display (not shown) outside of the patient. The balloon may then be inflated until it exerts a predetermined pressure on the cardiac orifice/esophagus. Alternatively or additionally, an endoscope may be used to view the restricted cardiac orifice/esophagus and the pressure sensor 1200 may include a light to facilitate viewing by the endoscope. Alternatively, the restricted cardiac orifice/esophagus may be gauged by insertion of catheters of increasing outer diameters until the catheter is obstructed.

FIGS. 13A-13D illustrate a method for determining the diameter of the cardiac orifice/esophagus at different inflation levels of the balloon using a barium swallow. The balloon may be inflated to a first size. The patient may be then given a barium sulfate suspension to drink. Fluoroscopy images are taken as the barium suspension is swallowed. As the patient swallows the barium suspension, it coats the esophagus and cardiac orifice walls with a thin layer of the barium which is visible to x-rays. The barium coat enables the hollow structures of the esophagus and/or cardiac orifice to be imaged. The balloon may be then inflated to a second larger size and the barium swallow repeated until the cardiac orifice/esophagus is restricted to a predetermined diameter. Alternatively, the restricted cardiac orifice/esophagus may be imaged using an MRI machine.

Figure 14B:
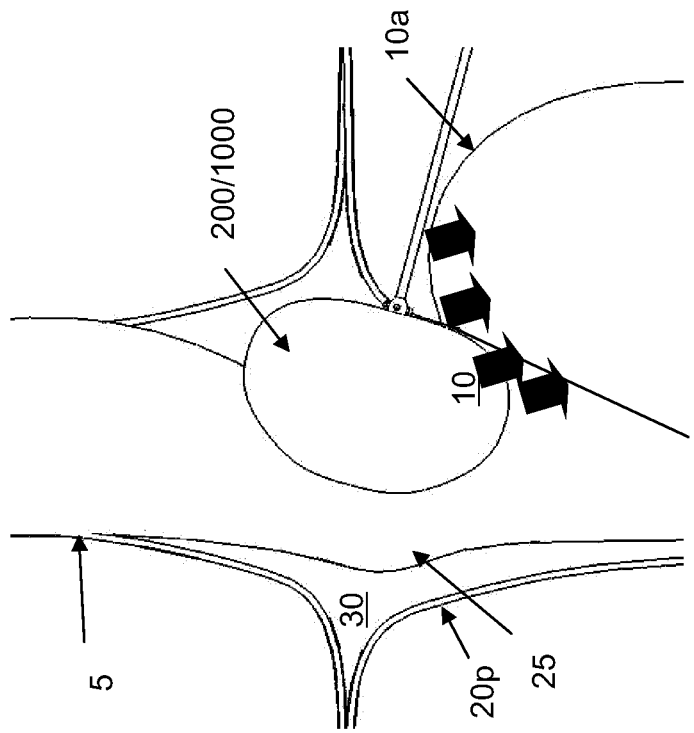
FIGS. 14A-14B illustrate an additional use for the balloon in treating obesity, according to another embodiment of the present invention.
Figure 14A:
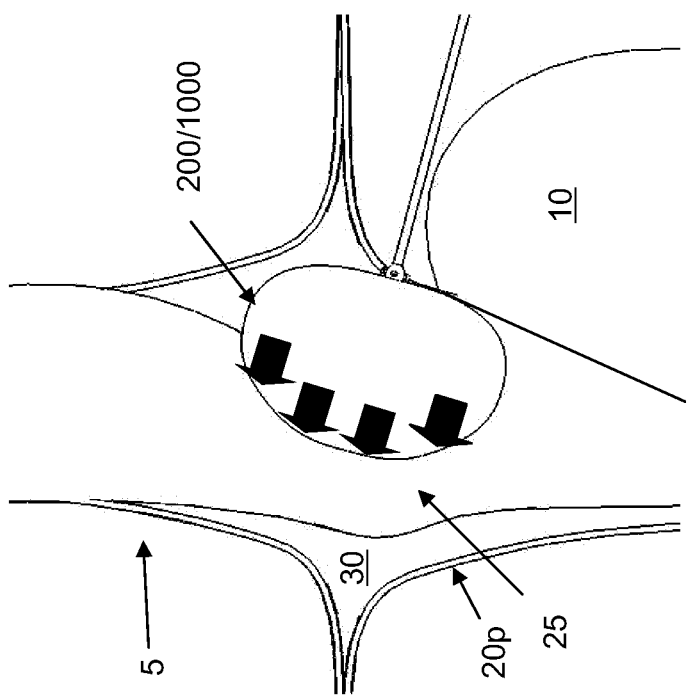

FIGS. 14A-14B illustrate an additional use for the balloon 200/1000 in treating obesity, according to another embodiment of the present invention. The balloon 200/1000 may be positioned and/or sized to additionally exert pressure on the stomach fundus 10a. While not wishing to be bound by theory, it is believed that exertion of pressure on the stomach fundus may reduce Ghrelin production, thereby reducing the patient's appetite. The pressure exerted may also act as the stimuli for the fundus 10a to signal the brain that the stomach is full. In another embodiment, the balloon may be further divided into three chambers. For example, the second chamber may be partitioned into second and third chambers where the third chamber faces the fundus. In this alternative, the first and third walls may have a lower or substantially lower stiffness than the second chamber and be independently inflated so that respective pressures exerted on the cardiac orifice and the fundus may be independently controlled.

In another alternative embodiment (not shown), one or more electrodes may be attached to an outer surface of the balloon so that inflation of the balloon causes the electrodes to contact nerve tissue of the patient. Wires may extend from the electrode into an additional lumen of the balloon catheter. The wires may provide electrical communication between the electrodes and a neuro-modulator. Electrical contact between the electrodes and the nerve tissue allows one or more electrical signals to be applied to the nerve tissue, wherein the electrical signals are sufficient to electrically neuromodulate the nerve tissue. For example, the nerve tissue may comprise at least one vagal trunk (i.e. the anterior and/or posterior vagal trunk) of the vagus nerve. For example, the electrical signals may at least partially block neural impulses in nerve tissue that innervates the stomach, such that the patient experiences decreased gastric motility, decreased gastric enzyme production, and/or decreased gastric acid production. In another embodiment, the electrical signals may stimulate the transmission of neural impulses, e.g., in nerve tissue that innervates the diaphragm, such that the patient experiences a sensation of satiety or fullness.

In one embodiment, the procedure for implanting the balloon into the GE space may be as follows. Initially, a working catheter is inserted through the trocar to a location between the stomach and the diaphragm. Then, the sleeve retaining the hooks is actuated to push the hooks out of the working catheter and grasp the POL. The sleeve is pulled/twisted to separate the POL from the GE space tissue and form an opening in the POL. In another embodiment, the working catheter is pulled back to separate the POL from the GE space tissue. After separation, a puncture tool is inserted through the working catheter to create an opening in the POL for the insertion of the balloon. In another embodiment, the balloon puncture tool may be provided on the balloon, the hook sleeve, or the working catheter. The puncture tool is retrieved after forming the opening. Thereafter, the balloon is inserted through the opening to the proper location for implantation. The balloon may be guided by the inner catheter. In another embodiment, the inner catheter may be pre-positioned adjacent the puncture tool so that the entire process may be performed in one trip. After being placed at the proper location, the balloon is inflated to exert a pressure on one portion of the esophagus/cardiac orifice, thereby constricting the lumen in the esophagus/cardiac orifice. Additionally, the balloon may be inflated and/or positioned such that the balloon may also apply a pressure against the stomach. The inflated balloon may be anchored to the POL using hooks, staples, or sutures. After inflation, the inner catheter, the sleeve, and the working catheter are retrieved. The balloon catheter remains and is provided with an injection port that may be attached to the skin, either internally or externally. The valve manifold may connect to the injection port for inflation or deflation of the balloon.

FIGS. 15A, 15C, and 15D illustrate a method for implanting an electrode 1560 for treating obesity, according to another embodiment of the present invention. FIG. 15A is a sectional view of a patient cut through the diaphragm 15. FIGS. 15C and 15D are isometric views of a portion of the GI tract. A catheter 1540 may be inserted laterally (FIG. 15A) adjacent or through the diaphragm 15 and through the POL 20p at a location so that the electrode may be inserted between the aorta 1510a (next to the vertebral column 1505v) and the esophagus/cardiac orifice 5,25. The catheter may include hooks for tearing an opening through the POL, as discussed above with reference to FIGS. 6A-7C. Alternatively, the catheter 1540 may be inserted anteriorly (FIG. 15B) using using one or more trocars 405,410 (see FIGS. 4A and 4B). The catheter 1540 may be inserted through the POL 20p between the diaphragm 15 and the esophagus/cardiac orifice 5,25. An electrode assembly 1550 may then be inserted through catheter 1540 and into the GE space 30.

The electrode assembly 1550 may include a lead conduit 1555 connected to a paddle electrode 1560. The electrode assembly 1550 may be inserted until the paddle electrode 1560 is received at least partially, substantially, or wholly within the GE space 30. One or more pairs of electrodes 1561,1562 of the paddle electrode 1560 may contact or be closely proximate to the posterior vagal trunk 1515*b*, thereby providing electrical communication between the posterior vagal trunk and the electrodes. The paddle electrode 1560 may be located so that a first electrode pair 1561 proximate the lead conduit is in contact or close proximity with the posterior vagal trunk. Additionally, the paddle electrode or lead conduit may be secured to the POL 20*p*, such as discussed above with respect to FIGS. 9B and 9D. Alternatively or additionally, the paddle electrode may be located in the GE space so that the electrodes are in close proximity or contact with diaphragmatic muscle so that minor nerves embedded in the muscle may be modulated. The anterior vagal trunk 1515*a*, spinal cord 1505*c*, and vena cava 1510*v* are also illustrated. Alternatively, the catheter may be a dilator inserted using a guide wire and one or more dilators as discussed below.

FIGS. 16A and 16B illustrate a neuromodulator 1590. The electrode assembly 1550 may be part of the neuromodulator 1590. The neuromodulator 1590 may further include a generator 1570. The generator 1570 may be implanted in the patient's body, such as in a pocket formed by the implanting surgeon just below the skin in the abdomen. The generator 1570 may be in electrical communication with the pairs of electrodes via lead wires housed in the lead conduit. The generator may be operable to deliver a signal to the posterior vagal trunk 1515*b*, thereby stimulating the nerve and promoting a feeling of satiety. Alternatively, the generator 1570 may deliver the signal to the posterior vagal trunk 1515*b* to inhibit or block the nerve.

The generator 1570 may include a housing, a microprocessor controller, a battery, an inverter or pulser, an antenna, and a transceiver. The housing may be sealed and made from a biocompatible material, such as titanium. The controller may operate the inverter or pulser to deliver the output signal according to predetermined instructions. The controller may be reprogrammed by wireless communication with an external computer (not shown) via the antenna and receiver. The generator may further include a battery charger operable to generate electricity from wireless signals and recharge the battery. Alternatively, the generator may be worn by the patient externally and the lead conduit may extend percutaneously to the implanted electrodes. Alternatively, the generator may include only a housing, an antenna, a receiver, and an RF generator and deliver the signal to the electrodes when powered wirelessly, analogously to a passive RFID tag. The inverter or pulser may supply the signal to the electrodes and may supply a pulse or sinusoidal wave. A voltage, frequency, and/or current of the signal may be varied. For example, to stimulate the vagal nerve, the pulser may deliver pulses having a width of 0.05-1.5 ms, a current of 0.1-1.5 mA, a frequency of 5-150 Hz for a period of 300-10,000 sec.

The other pair 1562 of electrodes may be used as sensors so that the modulator controller may detect natural activity along the vagal nerve. The controller may modulate the vagal nerve in response to detected activity, such as that indicative of eating. Each electrode pair 1561, 1562 may be in communication with the generator via a respective pair of lead wires. Alternatively, an intensity of the pulses may be increased so that the electrode pair 1561 also modulates the diaphragmatic muscle, splanchnic nerve and/or the celiac ganglia.

Figure 17:
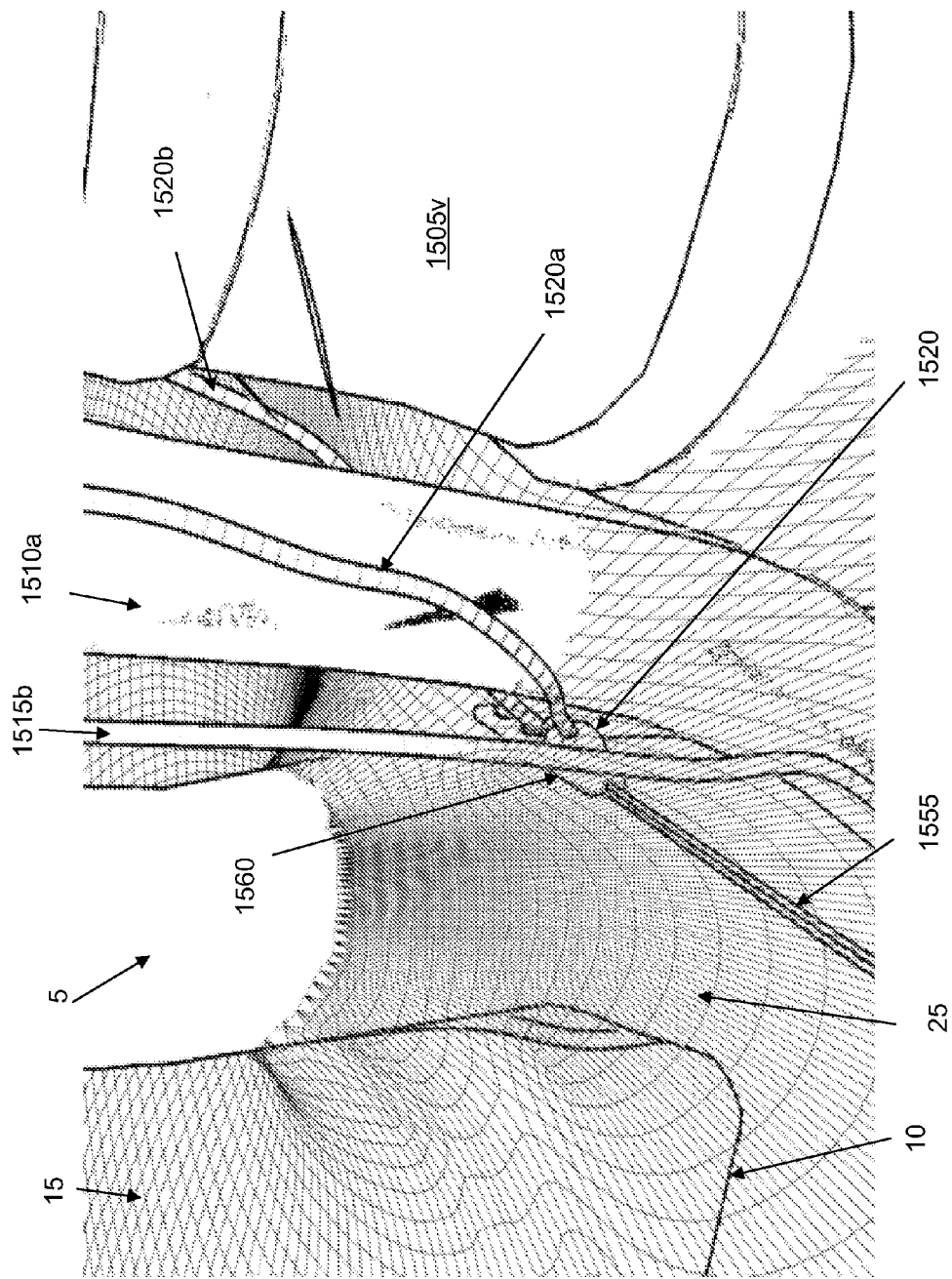
FIG. 17 illustrates an alternative placement of the paddle electrode, according to another embodiment of the present invention.

FIG. 17 illustrates an alternative placement of the paddle electrode 1560, according to another embodiment of the present invention. The paddle electrode 1560 may be implanted so that the first electrode pair is in close proximity or contact with the posterior vagal nerve and the second electrode pair is in close proximity or contact with the left splanchnic nerve 1520*a*, celiac ganglia 1520, and/or right splanchnic nerve 1520*b*. In this manner, the modulator controller may selectively modulate (i.e., stimulate or block) the anterior vagal nerve 1515*b* by energizing the first electrode pair, thereby creating/blocking a parasympathetic response or the celiac ganglia/splanchnic nerves by energizing the second electrode pair, thereby creating/blocking a sympathetic response, as desired to treat obesity or other eating disorders, such as bulimia and anorexia. In order to accomplish electrical communication with vagal and splanchnic/celiac ganglion, the paddle electrode may be disposed partially, within the GE space 30 so that the first electrode pair is in contact/close proximity with the vagal nerve and partially through the POL so that the second electrode pair is in close proximity/contact with the splanchnic nerve/celiac ganglion.

Alternatively, the paddle electrode may be disposed substantially or wholly within the GE space so that the second pair is only in close proximity to the splanchnic nerve/celiac ganglion. Alternatively, the paddle electrode may be wholly disposed along an exterior surface of the POL or secured and/or supported to/from the POL so that the electrode pair is contact/close proximity with the splanchnicnerve/celiac ganglion or other adjacent tissue. Alternatively, the paddle electrode may be in electrical communication with only one of the splanchnic nerves, both of the splanchnic nerves, and/or the celiac ganglia. Alternatively or additionally, the electrode may be extended or repositioned so that an electrode pair is in close proximity or contact with the diaphragmatic muscle, as discussed above. Alternatively, the paddle electrode may include one or more pairs of electrodes and the pairs may be in close proximity with the posterior vagal nerve, the splanchnic nerve, diaphragmatic muscle, and/or the celiac ganglia so that energization of the electrodes indiscriminately modulates the nerves.

FIGS. 18A and 18B illustrate implanting a balloon electrode 1860, according to another embodiment of the present invention. The balloon electrode 1860 may be implanted in a manner similar to that illustrated in FIGS. 15A-D, discussed above, so that the balloon electrode may be substantially or wholly disposed in the GE space. The balloon electrode may be similar to the paddle electrode 1560 except that a balloon 1565 is disposed on a surface of the paddle opposite to the electrode surface of the paddle. The balloon may be made from one of the materials discussed above for the balloon 200 and inflated with one of the fluids discussed above for the balloon 200. The lead conduit 1855 may further include a catheter (not shown) for inflation of the balloon. The balloon may be bonded to the paddle surface, such as molding thereto or using an adhesive. Inflation of the balloon may improve contact with the anterior vagal nerve and/or diaphragmatic muscle and restrict the esophagus/cardiac orifice as discussed above in relation to the balloon 200, thereby providing a dual prong treatment for obesity.

FIGS. 19A and 19B illustrate the electrode assembly 1850 in deflated and inflated positions, respectively. The electrode assembly may be part of a neuromodulator, similar to the neuromodulator 1590. The neuromodulator may include a generator (not shown) similar to the generator 1570. The generator may further include an electric pump to inflate the balloon and a reservoir to store inflation fluid. The generator may include a pressure sensor for monitoring a volume of the balloon. In this manner, the generator may inflate the balloon to a predetermined pressure and then a restricted diameter of the esophagus/cardiac orifice may be determined as discussed above. A new pressure may then be communicated wirelessly to the implanted generator and the generator may respond by inflating/deflating the balloon appropriately to optimize constriction of the esophagus. Alternatively, the generator may be worn by the patient externally and the generator may include an external fill port and a valve, thereby allowing an external pump or syringe (not shown) to be connected for inflating/deflating the balloon.

Figure 20B:
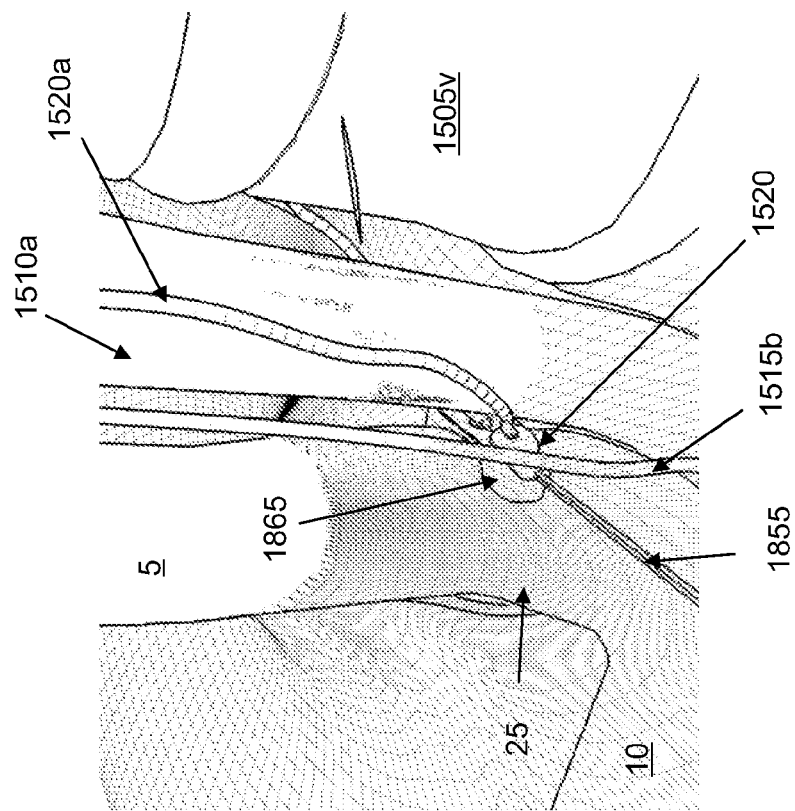
FIGS. 20A and 20B illustrate an alternative placement of the balloon electrode, according to another embodiment of the present invention.
Figure 20A:
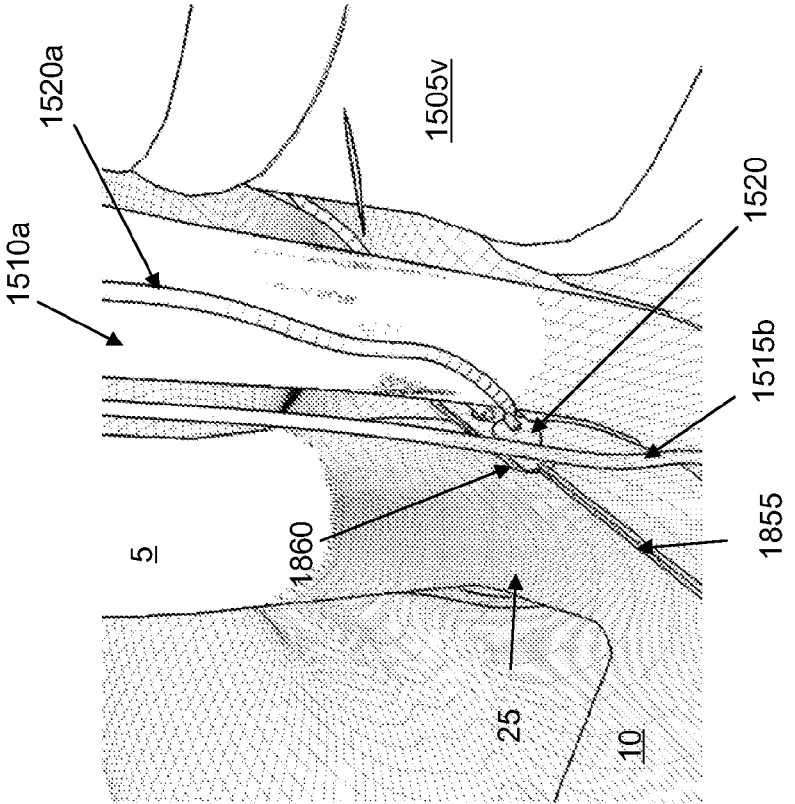
Figure 21D:
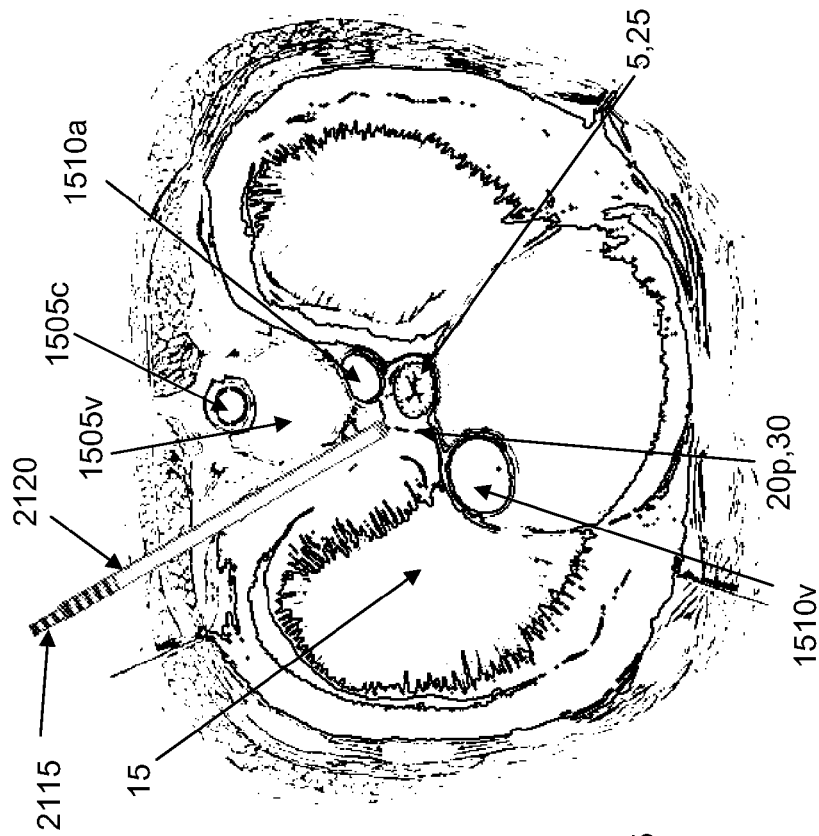
Figure 21C:
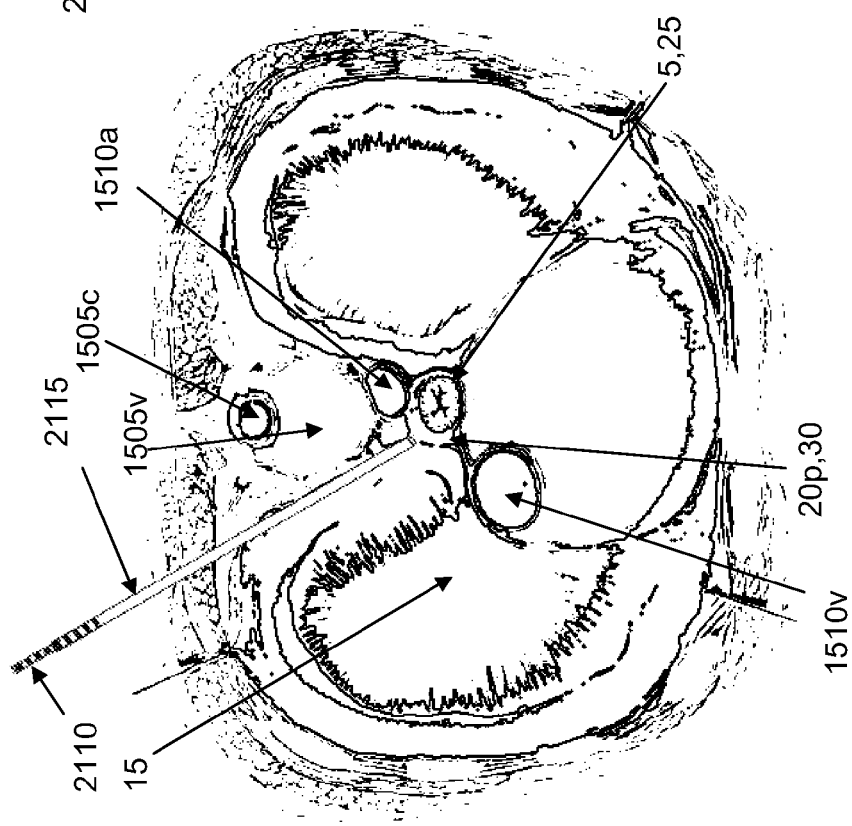
Figure 21E:
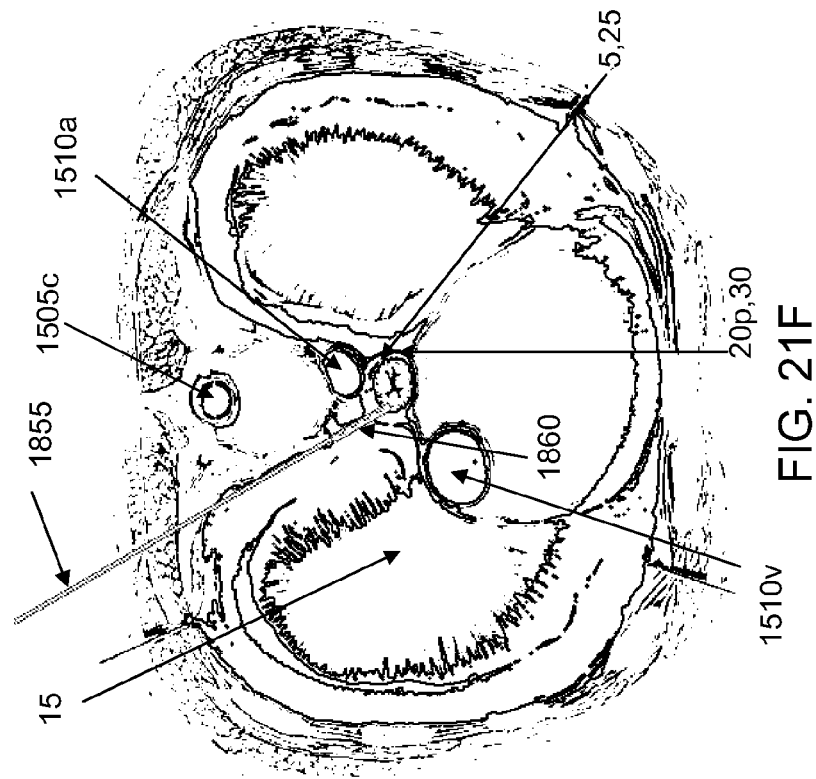
Figure 21F:
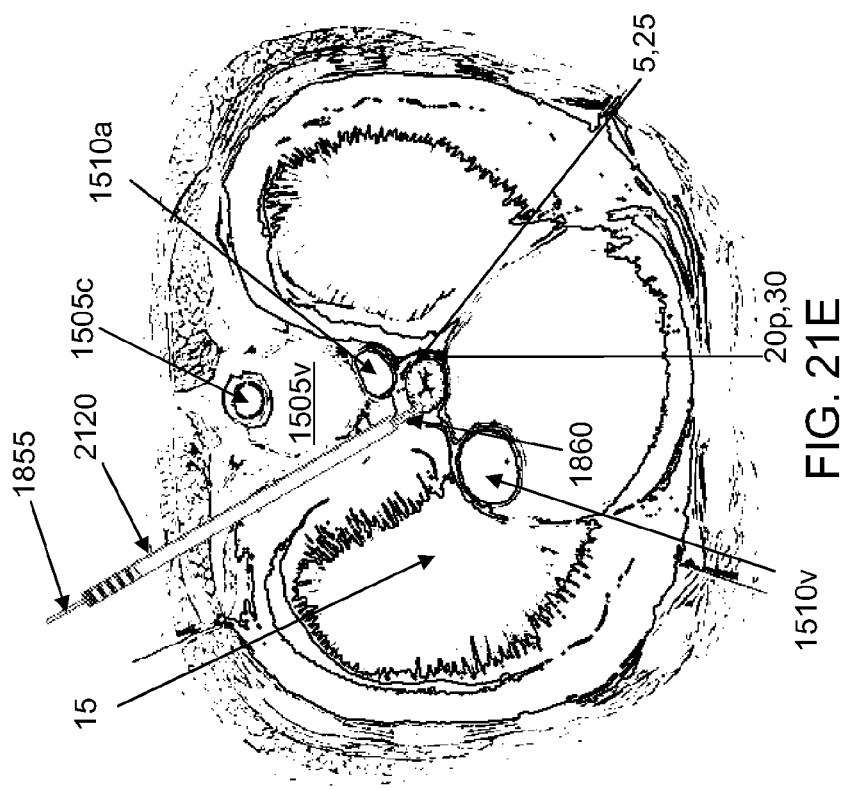
Figure 21G:
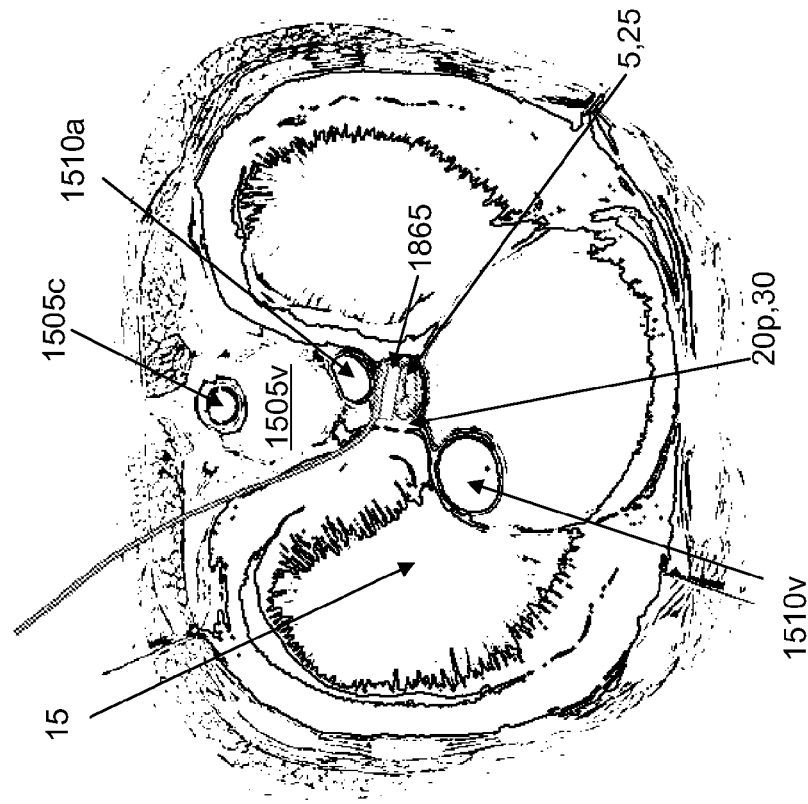
Figure 21H:
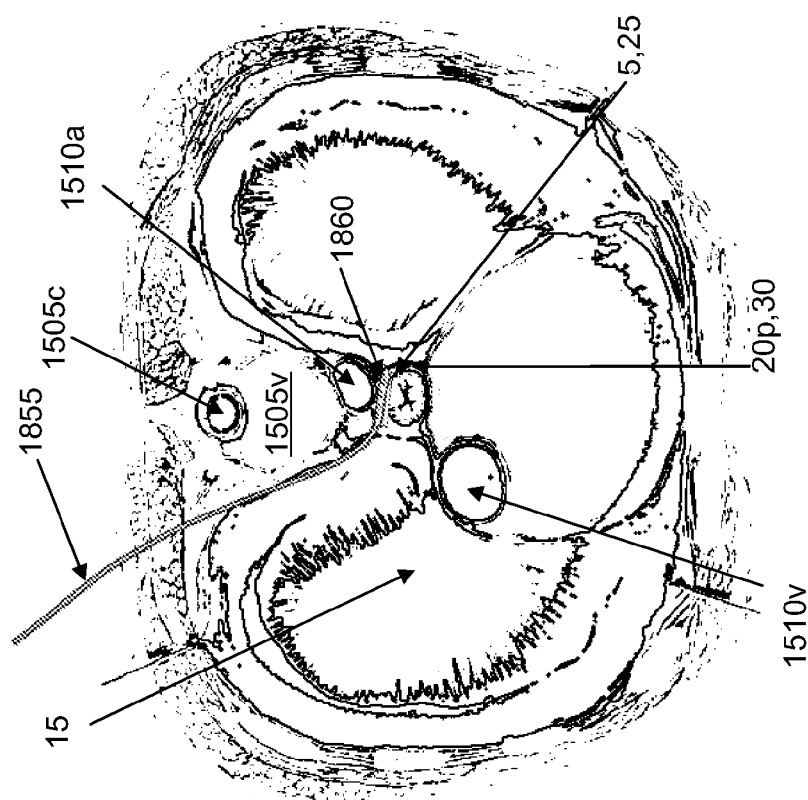

FIGS. 20A and 20B illustrate an alternative placement of the balloon electrode 1860, according to another embodiment of the present invention. Similar to the FIG. 17 alternative, the balloon electrode may be placed in electrical communication with the anterior vagal and ganglia/splanchnic nerves to selectively modulate the nerves in addition to constricting the esophagus.

FIGS. 21A-H illustrate an alternative method for implanting the balloon electrode, according to another embodiment of the present invention. A guide wire may be inserted posteriorly between the vertebral column and the diaphragm and through the POL 20p. The insertion may be to the right of the vertebral column (shown) or to the left. A first dilator 2110 may then be slid over the guide wire to enlarge the opening. The guide wire may then be removed. A second dilator 2115 may then be slid over the first dilator to further enlarge the opening. The first dilator may then be removed. A third dilator 2120 may then be slid over the second dilator. The second dilator may then be removed. The balloon electrode assembly 1850 may then be inserted through the third dilator. The third dilator may then be removed. A distal end of the lead conduit may be pre-formed into an L-shape so that the balloon electrode is biased toward a position in the GE space 30 between the cardiac orifice/esophagus and the aorta. Alternatively, the balloon electrode assembly may be steerable. Once the balloon electrode assembly is in position, the balloon may be inflated, thereby restricting the esophagus/cardiac orifice and firmly pressing the electrodes into engagement with the nerves. The balloon electrode may be implanted vertically at either location, discussed above in relation to FIGS. 18 and 20. Alternatively, the paddle electrode 1560 may be used instead of the balloon electrode 1860.

Figures 22A, 22B:
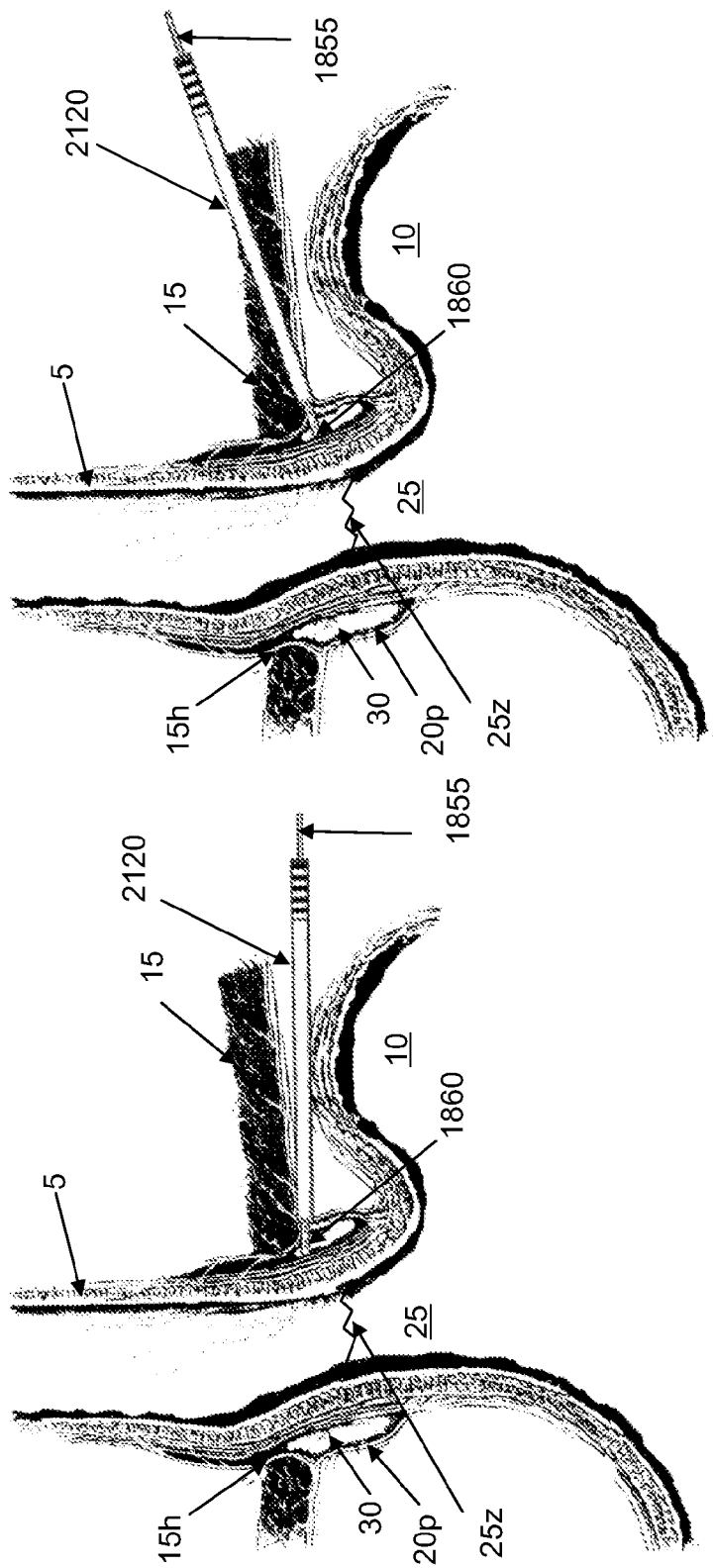
FIGS. 22A and 22B are views of a portion of the GI tract illustrating possible approaches for the posterior insertion of FIGS. 21A-H.

FIGS. 22A and 22B are views of a portion of the GI tract illustrating possible approaches for the posterior insertion of FIGS. 21A-H. The wire, dilators, and catheter assemblies may inserted through the POL along a horizontal path proximately below the diaphragm and between the diaphragm and the stomach. Alternatively, the wire, dilators, and catheter assemblies may inserted through the diaphragm and the POL along an inclined path.

Figures 23A, 23B:
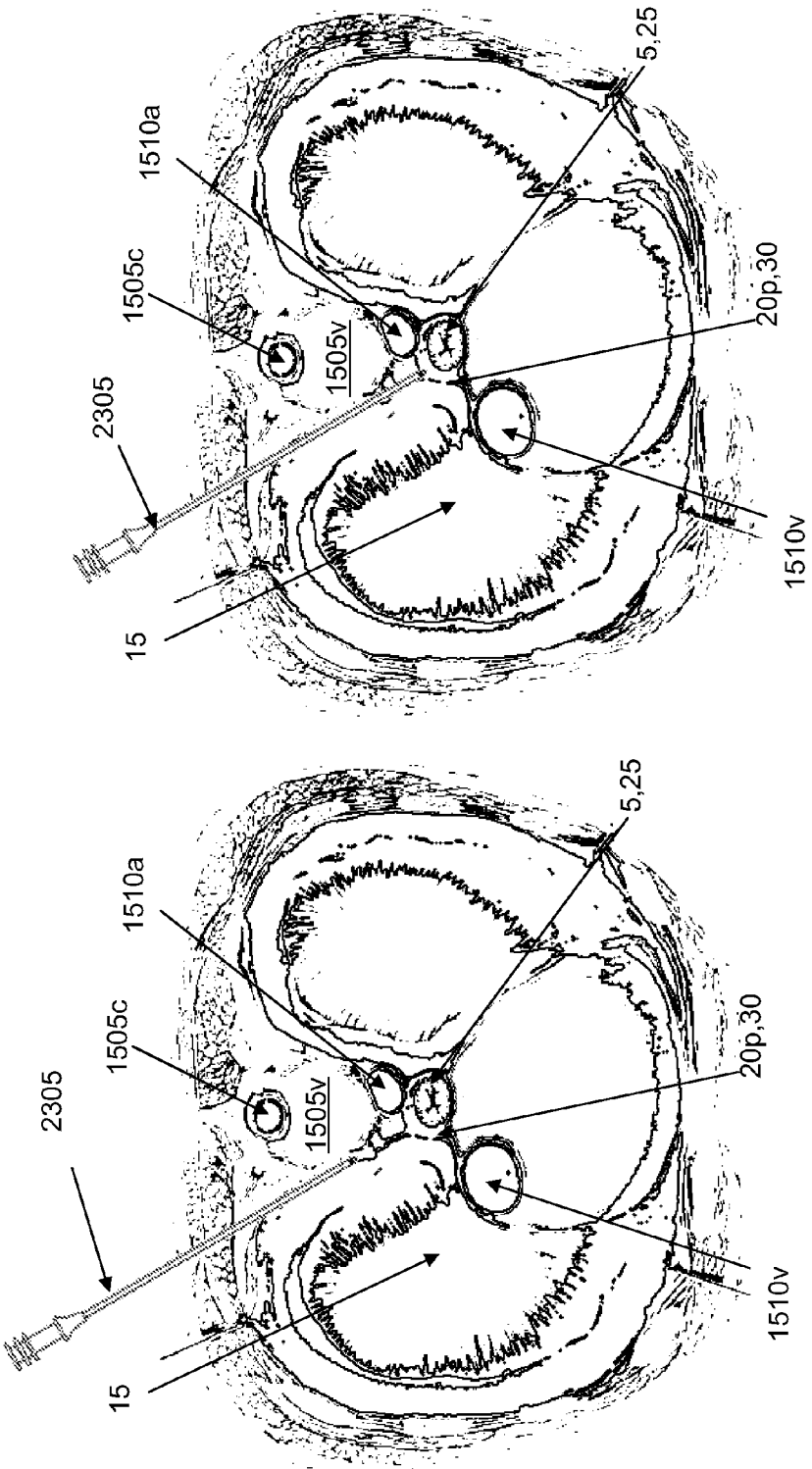
FIGS. 23A-23F illustrate posterior implantation of a catheter electrode 2350, according to another embodiment of the present invention.
Figures 23C, 23D:
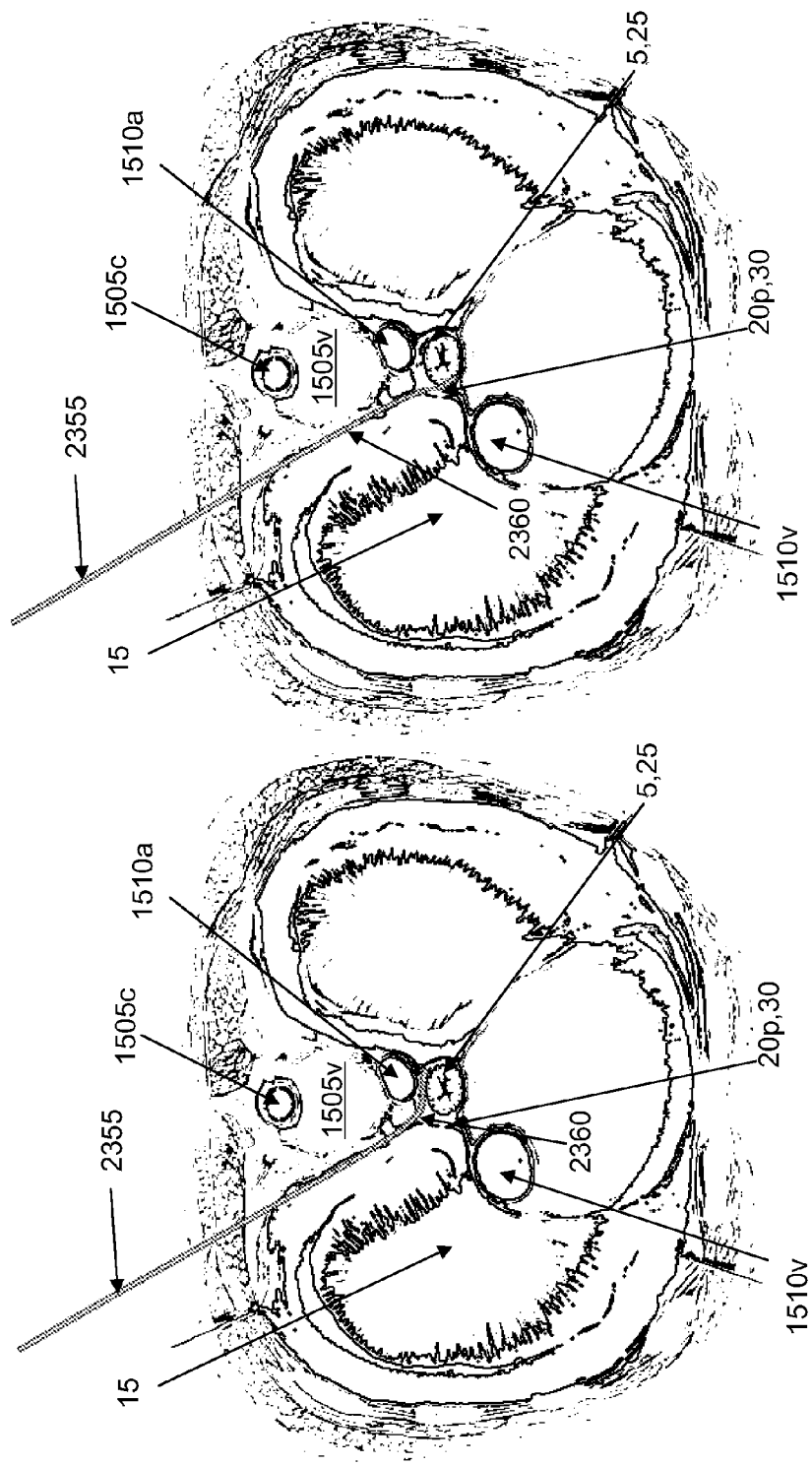
Figure 23F:
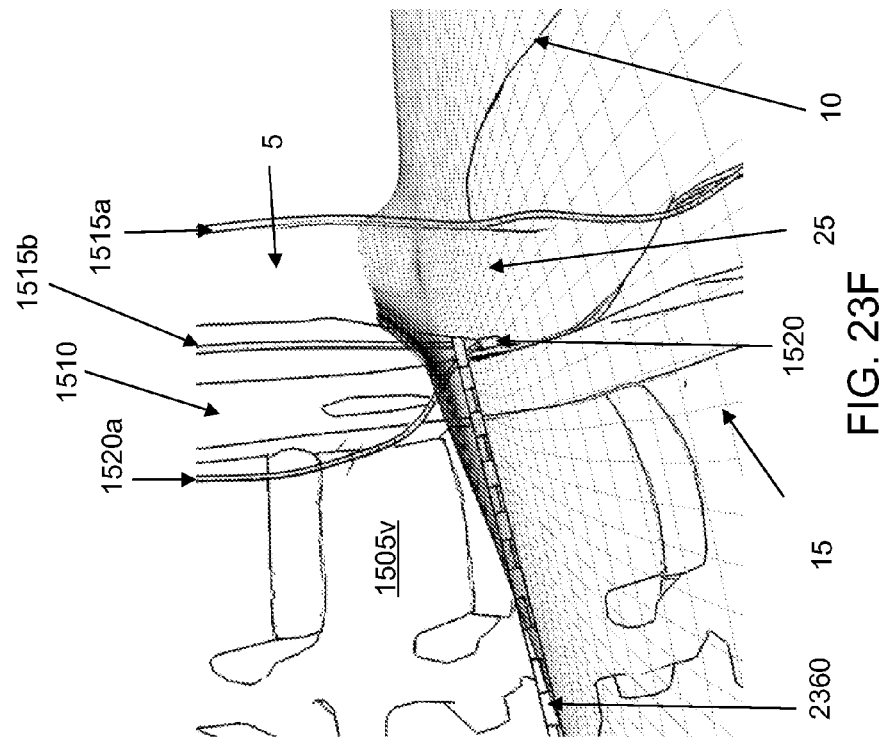
Figure 23E:
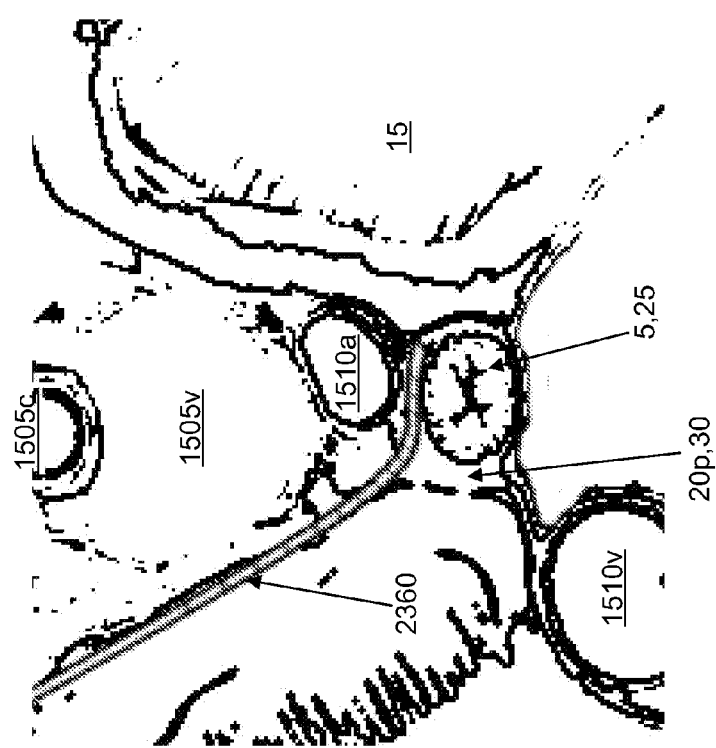

FIGS. 23A-23F illustrate posterior implantation of a catheter electrode 2350, according to another embodiment of the present invention. A spinal needle 2305 may be inserted posteriorly into the diaphragm proximate to the vertebral column and through the POL. The catheter electrode may then be inserted through the spinal needle and into the GE space. As a tip 2360 of the catheter electrode 2350 exits the spinal needle, the tip may be steered toward a posterior portion (FIGS. 23C, 23E, and 23F) of the cardiac orifice/esophagus or toward an anterior portion of the cardiac orifice/esophagus (FIG. 23D). As with the paddle/balloon electrodes, the catheter electrode may be implanted so that a first electrode pair is in close proximity or contact with the posterior vagal nerve and the second electrode pair is in close proximity or contact with the left splanchnic nerve 1520a, celiac ganglia 1520, and/or right splanchnic nerve 1520b. In this manner, the modulator controller may selectively modulate (i.e., stimulate or block) the anterior vagal nerve 1515b by energizing the first electrode pair, thereby creating/blocking a parasympathetic response or the celiac ganglia/splanchnic nerves by energizing the second electrode pair, thereby creating/blocking a sympathetic response, as desired to treat obesity. Alternatively, the catheter electrode may be implanted laterally or anteriorly. Alternatively, the catheter electrode may be placed in contact/close proximity with only the vagal nerve, the diaphragmatic muscle, or both.

Figures 24A, 24B:
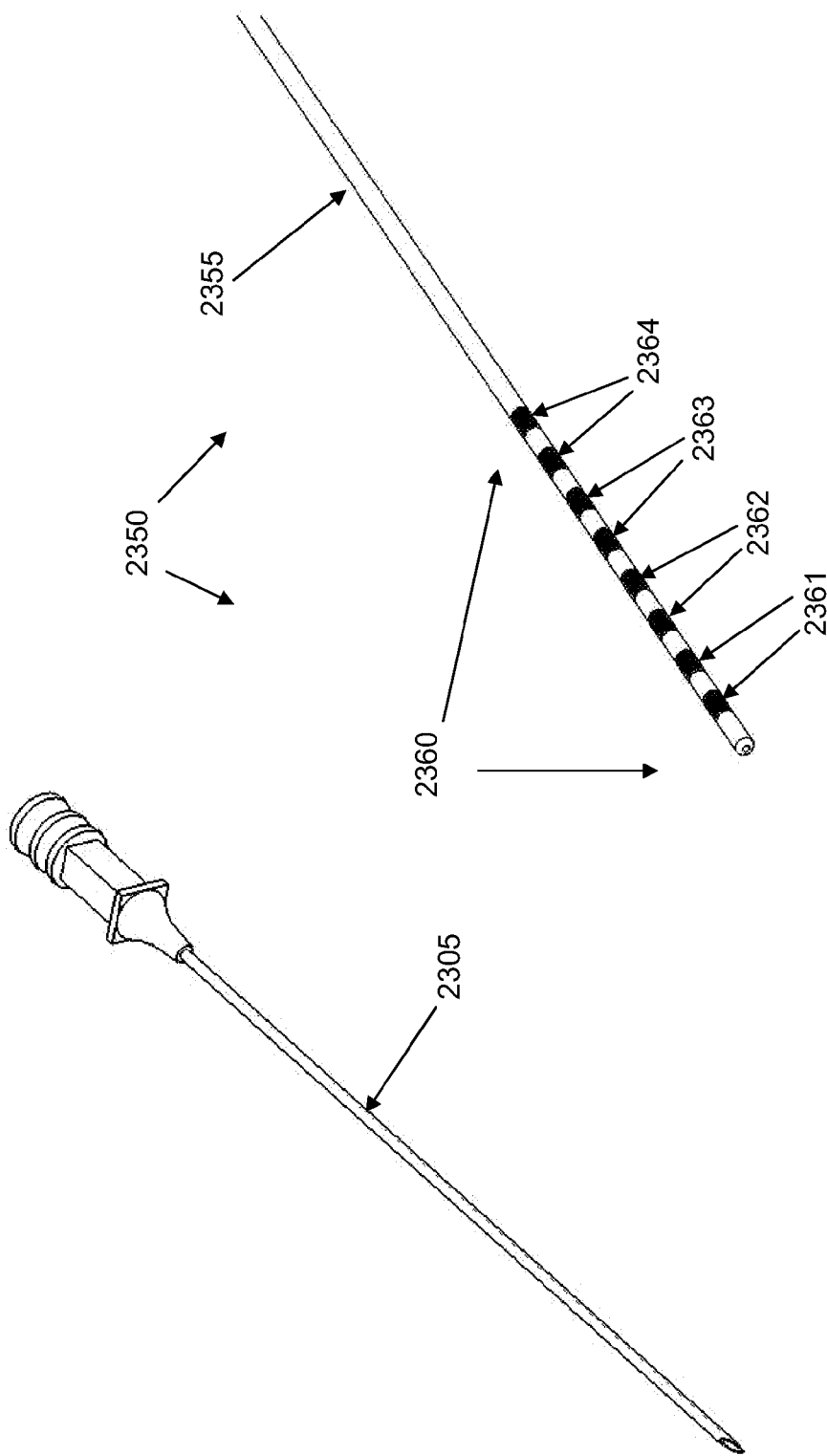
FIG. 24A illustrates the spinal needle.
FIG. 24B illustrates the catheter electrode.

FIG. 24A illustrates the spinal needle 2305. FIG. 24B illustrates the catheter electrode 2350. The catheter electrode 2350 may include an elongated lead conduit 2355 having proximal and distal ends, a tip 2360 at the distal end of the lead conduit 2355, and a control handle (not shown) at the proximal end of the lead conduit 2355. A suitable control handle is discussed and illustrated in U.S. Re. 34,502, which is herein incorporated by reference in its entirety.

The lead conduit 2355 may include an elongated tubular construction section having a single lumen. The lead conduit 2355 may be flexible, i.e., bendable, but substantially non-compressible along its length. The lead conduit 2355 may made from a biocompatible material, such as a nylon tube surrounded by braided stainless steel with a polyurethane coating. The tip 2360 may include a short section of flexible tubing having a pair of nonoverlapping, e.g., side-by-side first and second lumens which are eccentric, i.e., are not coaxial with the tip 2360. The tubing may be made from a material more flexible than the lead conduit 2355, such as polyurethane.

One or more pairs 2361-2364 of electrodes may be disposed along a length of the tubing. The electrodes may be rings made from an electrically conductive and biocompatible material, such as a metal or alloy. An outer diameter of the electrodes may be about the same as the outer diameter of the tubing so that the electrodes form a smooth, continuous outer surface with the outer surface of the flexible tubing. Lead wires may extend from the control handle through the lumen of the lead conduit 2355 and into the second lumen of the tip 2360. Each lead wire may be attached to a respective electrode. A distal end of the flexible tubing may be rounded to serve as a guide nose. The proximal end of the tip 2360 may include an outer circumferential notch and the distal end of the lead conduit 2355 may include an inner circumferential notch. The notches may be sized to form a snug fit. The tip 2360 may then be bonded to the lead conduit, such as with an adhesive.

A puller wire may extend from the control handle through the lumen of the lead conduit 2655 and into the first lumen of the tip 2360. The puller wire may be made from a metal or alloy, such as stainless steel. The puller wire may extend into the first lumen of the tip 2360 to a position near the distal end of the tip and may be attached to the wall of the flexible tubing. The puller wire may be surrounded by a sheath for lubricity and to keep the puller wire generally coaxial with the lead conduit 2355. The sheath may be made from a polymer, such as PTFE. The sheath may be swaged in the first lumen to accommodate the smaller first lumen of the tip 2360.

The control handle may include a tubular housing having a piston chamber formed at the distal end of the housing and a connector chamber formed at the proximal end of the housing. A longitudinal passage and an offset passage may lead from the piston chamber to the connector chamber. The housing may be generally symmetrical about its longitudinal axis. A cylindrical piston may be slidably disposed within and generally coaxial with the piston chamber. A seal, such as an o-ring may be disposed in an outer surface of the piston and engage an inner surface of the housing.

The piston may have a slot extending along an outer surface thereof. A fastener may extend through a wall of the housing and into the slot, thereby allowing longitudinal movement of the piston relative to the housing while keeping the piston coupled to the housing. The piston may have a longitudinal bore formed therethrough. The lead conduit 2355 may extend into the piston bore and may be bonded to the piston, such as by an adhesive. The distal end of the piston may extend beyond the distal end of the housing. An annular thumbrest may be attached to the distal end of the piston to facilitate longitudinal movement of the piston.

The puller wire may extend through the piston bore and may be attached to the housing by an anchor. The anchor may extend into a transverse hole in the portion of the housing between the connector chamber and piston chamber. The anchor may block the longitudinal passage, but not the offset passage. The anchor may be rotatable within the hole, but may fit snugly so that it does not rotate freely. The anchor may include a transversely extending hole which may be rotated into alignment with the longitudinal passage. The puller wire may pass through the longitudinal passage and anchor hole and wedged between the anchor and the wall of the housing. Tension on the puller wire may be adjusted by rotation of the anchor.

The lead wires may extend from the lead conduit 2355 proximally through the piston bore, the piston chamber, the offset passage between the piston and connector chambers, and into the connector chamber. A sheath may surround and protect the lead wires in the piston chamber, offset passage and connector chamber. The lead wires and sheath may be bowed or looped in one of the chambers to provide slack. In the connector chamber, the lead wires may be connected to a rotary connector. The rotary connector may include a cylindrical male plug extending proximally from the control handle housing coaxially with the housing. The plug may have a series of electrical contacts or terminals along its length, each of which is electrically connected to a separate lead, and, therefore, a separate lead wire, within the connector chamber. The plug may be connected with the modulator generator (discussed above). An annular flange may secure the rotary connector to the housing and may seal the proximal end of the connector chamber. A vent may lead from the connector chamber. The vent may be through the housing wall, flange or through the plug of the rotary connector.

In use, the tip 2360 may be curved or bent to steer the tip by gripping the control handle housing and moving the piston distally out of the piston chamber by pushing outwardly on the thumbrest. This action may cause movement of the puller wire relative to the lead conduit 2355 and tip 2360, effectively pulling the tip 2360 proximally toward the control handle. Because the puller wire may be offset from the axis of the tip 2360, the tip may bend in the direction of the offset, to accommodate the force exerted on it.

FIGS. 25A and 25B illustrate posterior endoscopic implantation of the catheter electrode 2350, according to another embodiment of the present invention. The opening through the POL may be formed using the guide wire and dilators, as discussed above. A tube 2555 of the endoscope may then be inserted through the third dilator 2120. The tube may conduct an image of the GE space to the surgeon to facilitate implantation of the catheter electrode.

Figure 26B:
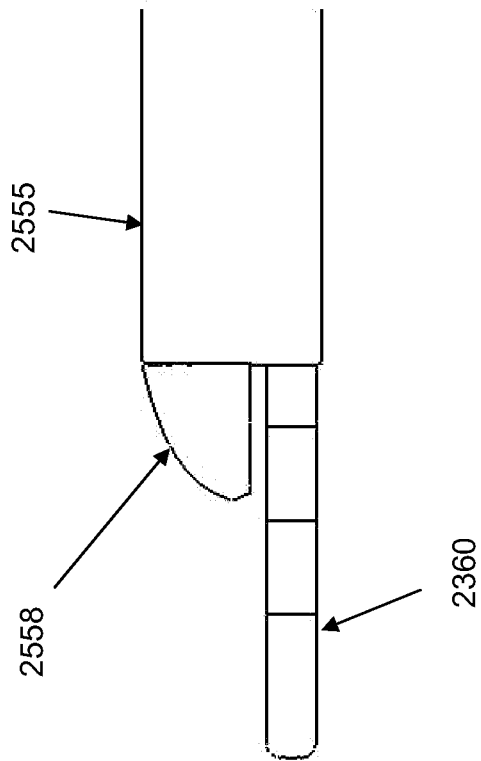
FIGS. 26A and 26B illustrate a distal end of the endoscope tube.
Figure 26A:
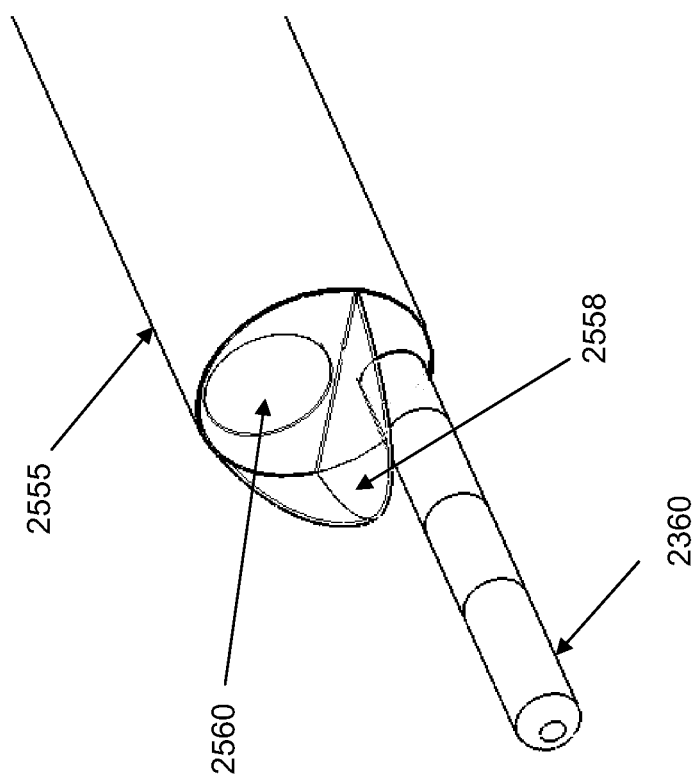

FIGS. 26A and 26B illustrate a distal end of the endoscope tube 2555. The endoscope may include a head 2550 having a bore 2550b for receiving an optical cable and a side port 2550p for receiving the catheter electrode. The endoscope may further include a light source. The endoscope may further include the tube 2555 having dual lumens (i.e., concentric or eccentric) connected to the head 2550. An optical lumen may conduct the optics and a working lumen may conduct the catheter electrode. The tube may be rigid or flexible and the endoscope may be analog or digital. If rigid, the optical lumen may house an optical fiber bundle for conducting light from the light source to illuminate the object and a lens system for conducting the object image from the lens 2560 to an eyepiece or video processor. If the tube is flexible, then a second fiber bundle may replace the lens system (analog) or an image sensor (i.e., CCD or CMOS) may capture and convert the image to an electrical signal and an AFE may digitize the signal and send the signal to the video processor via an electrical cable.

The endoscope tube 2555 may further include a nose 2558 to protect the lens 2560 and guide the tube 2555. The nose 2558 may be made from a transparent and biocompatible material, such as glass, laminated glass, or a polymer, such as polycarbonate or acrylic. The nose 2558 may be quarter-ellipsoid or quarer-spherical in shape. The nose 2558 may be bonded to the distal end of the tube, such as with an adhesive.

Figure 27A:
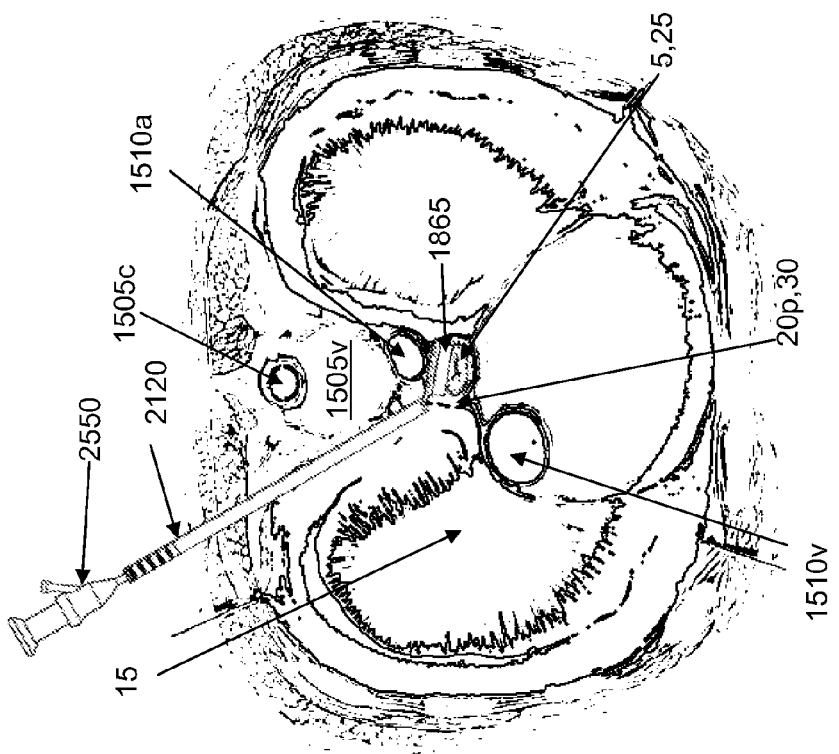
FIGS. 27A and 27B illustrate posterior endoscopic implantation of the balloon electrode, according to another embodiment of the present invention.
Figure 27B:
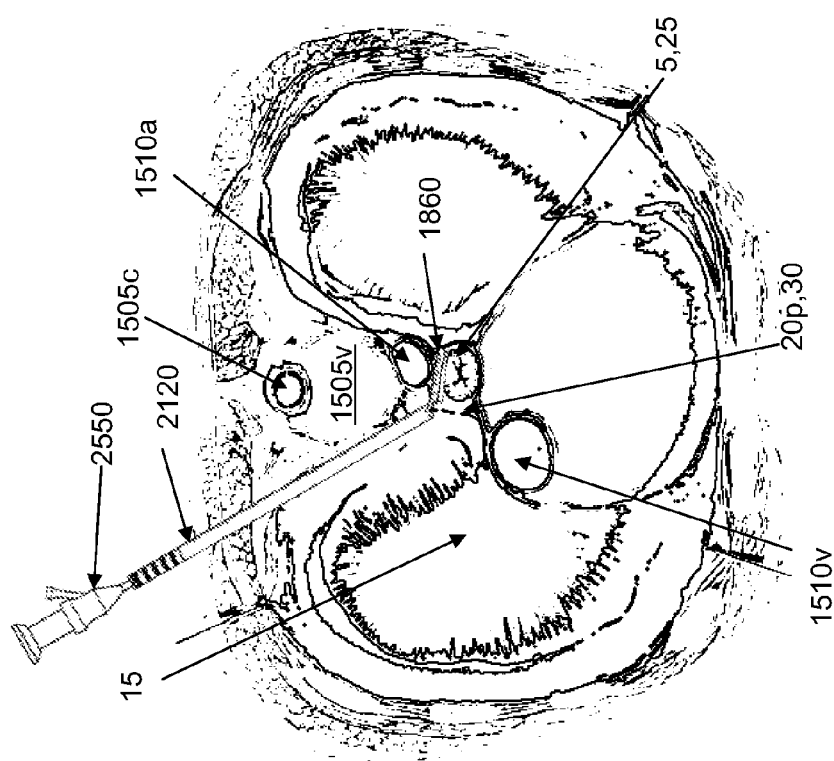

FIGS. 27A and 27B illustrate posterior endoscopic implantation of the balloon electrode 1860, according to another embodiment of the present invention. The opening through the POL may be formed using the guide wire and dilators, as discussed above. The endoscope tube 2555 may then be inserted through the third dilator 2120. Once implanted into the GE space, the balloon may be inflated to restrict the cardiac orifice/esophagus and ensure firm engagement of the electrodes with the target nerve(s).

Alternatively, the balloon, paddle, or catheter electrode may be implanted anteriorly using the endoscope and one or more trocars or laterally using the endoscope.

What is claimed is:

1. A minimally invasive method for treating a patient, comprising:
    advancing a working catheter from one of an abdomen or thorax to between a stomach and a diaphragm of the patient;
    engaging the phrenoesophageal ligament (POL);
    tearing at the POL to form an opening in the POL for introducing an electrode attached to an outer surface of a balloon at least partially into a gastroesophageal (GE) space formed between an inner wall of the POL and outer walls of an esophagus, a fundus of the stomach and a cardiac orifice;
    inflating the balloon; and
    modulating tissue using the electrode.

2. The method of claim 1, wherein the balloon and electrode are introduced substantially or wholly within the GE space.

3. The method of claim 1, further comprising securing the balloon and electrode to the POL.

4. The method of claim 3, wherein the balloon and electrode are secured to an interior portion of the POL.

5. The method of claim 3, wherein the balloon and electrode are secured to an exterior portion of the POL.

6. The method of claim 1, further comprising promoting a feeling of satiety in the patient during or after modulation.

7. The method of claim 1, wherein the tissue comprises a portion of the diaphragm.

8. The method of claim 7, wherein the tissue further comprises a portion of a nerve that innervates the diaphragm portion.

9. The method of claim 1, further comprising advancing the balloon and electrode within the GE space into a position adjacent a ventral aspect of a portion of the tissue.

10. The method of claim 9, further comprising passing a least a portion of the balloon and electrode out of the GE space towards a portion of the tissue.

11. The method of claim 10, further comprising passing at least a portion of the balloon and electrode in a dorsal direction out of the GE space towards a portion of the tissue.

12. The method of claim 1, wherein an inflated shape of the balloon is ellipsoid, ovoid, cylindrical, or polyhedral.

13. The method of claim 12, wherein:
the balloon comprises a first wall having a first stiffness, a second wall having a second stiffness, and a partition,
the first wall and the partition enclose a first chamber and the second wall and the partition enclose a second chamber, and
the second stiffness is substantially greater than the first stiffness.

14. The method of claim 1, wherein the working catheter, balloon and electrode are part of a catheter assembly, further comprising:
a balloon catheter disposed in the working catheter, and
a syringe or pump connected to the balloon catheter.

15. The method of claim 14, wherein the working catheter is part of an endoscope.

16. The method of claim 14, wherein the catheter assembly is steerable.

17. The method of claim 14, wherein the pump is electric and part of an implantable generator.

18. The method of claim 14, wherein:
the catheter assembly further comprises a wire preformed into a hook, and
the wire is operable between:
a first position where the wire is elastically restrained inside the working catheter, and
a second position where the wire returns to the preformed hook as the wire is extended from the working catheter.

19. The method of claim 14, wherein:
the catheter assembly further comprises:
an adapter connecting the balloon catheter and the balloon; and
a lug extending from an outer surface of the adapter, and
the method further comprises securing the lug to the POL.

20. The method of claim 1, where inflating the balloon further comprises:
expanding the balloon against the outer walls of the esophagus.

21. The method of claim 1, where inflating the balloon further comprises:
expanding the balloon against the fundus of the stomach.

* * * * *